US012643108B2

(12) United States Patent
Dev et al.

(10) Patent No.: US 12,643,108 B2
(45) Date of Patent: Jun. 2, 2026

(54) DEVICES AND METHODS FOR PARTICLE SOLUTION PREPARATION

(71) Applicant: IDEXX Laboratories, Inc., Westbrook, ME (US)

(72) Inventors: Arvind Dev, Scarborough, ME (US); Julie Rollins, South Portland, ME (US); Richard Holt, Old Orchard Beach, ME (US); Michael A. Schrameyer, Portland, ME (US); Richard Lemieux, Standish, ME (US); Nicholas Gustafson, South Portland, ME (US); Andrey Asanov, Buxton, ME (US)

(73) Assignee: IDEXX LABORATORIES, INC, Westbrook, ME (US)

( * ) Notice: Subject to any disclaimer, the term of this patent is extended or adjusted under 35 U.S.C. 154(b) by 700 days.

(21) Appl. No.: 18/078,528

(22) Filed: Dec. 9, 2022

(65) Prior Publication Data

US 2023/0184636 A1 Jun. 15, 2023

Related U.S. Application Data

(60) Provisional application No. 63/288,378, filed on Dec. 10, 2021, provisional application No. 63/288,386, filed on Dec. 10, 2021, provisional application No. 63/288,397, filed on Dec. 10, 2021, provisional application No. 63/288,408, filed on Dec. 10, 2021.

(51) Int. Cl.
| | |
|---|---|
| *G01N 1/28* | (2006.01) |
| *A61J 1/20* | (2006.01) |
| (Continued) | |

(52) U.S. Cl.
CPC .............. *B01L 9/06* (2013.01); *A61J 1/2096* (2013.01); *A61M 5/1782* (2013.01); *A61M 5/19* (2013.01);
(Continued)

(58) Field of Classification Search
None
See application file for complete search history.

(56) References Cited

U.S. PATENT DOCUMENTS

| | | | | |
|---|---|---|---|---|
| 5,484,524 A | * | 1/1996 | MacLaren | ............. B01F 25/312 |
| | | | | 261/DIG. 70 |
| 5,646,049 A | | 7/1997 | Tayi | |

(Continued)

FOREIGN PATENT DOCUMENTS

| | | |
|---|---|---|
| JP | 2013 072687 | 4/2013 |
| WO | WO2016168692 A1 | 10/2016 |

OTHER PUBLICATIONS

International Search Report and Written Opinion issued in International Application No. PCT/US2022/052374 dated Jul. 21, 2023.

(Continued)

*Primary Examiner* — Brian R Gordon
(74) *Attorney, Agent, or Firm* — McDonnell Boehnen Hulbert & Berghoff LLP

(57) ABSTRACT

A method for preparing an aliquot of solution is disclosed. The method includes agitating the solution with a baffle at a predetermined mixing speed to suspend the plurality of particles in the solution, wherein the baffle positioned at least partially within a vessel containing the solution, and wherein the vessel is engaged with a vessel receptacle configured to hold the vessel. The method also includes withdrawing, during the agitating, the aliquot of solution from the vessel with a pipette, such that an end of a pipette tip is positioned within the vessel.

10 Claims, 20 Drawing Sheets

(51) Int. Cl.

| | |
|---|---|
| *A61M 5/178* | (2006.01) |
| *A61M 5/19* | (2006.01) |
| *B01L 9/00* | (2006.01) |
| *B01L 9/06* | (2006.01) |
| *G01N 1/08* | (2006.01) |
| *G01N 1/10* | (2006.01) |
| *G01N 21/88* | (2006.01) |
| *G01N 33/543* | (2006.01) |
| *G01N 1/18* | (2006.01) |

(52) U.S. Cl.
CPC .................. *B01L 9/54* (2013.01); *G01N 1/08* (2013.01); *G01N 1/10* (2013.01); *G01N 1/2806* (2013.01); *G01N 21/8851* (2013.01); *G01N 33/54326* (2013.01); *A61J 2205/10* (2013.01); *B01L 2200/022* (2013.01); *B01L 2200/0605* (2013.01); *B01L 2300/021* (2013.01); *G01N 2001/185* (2013.01)

(56) References Cited

U.S. PATENT DOCUMENTS

| | | | |
|---|---|---|---|
| 6,270,249 | B1 | 8/2001 | Besuner et al. |
| 10,232,376 | B2 | 3/2019 | Capaccio et al. |

| | | | | |
|---|---|---|---|---|
| 2002/0051922 | A1* | 5/2002 | Yamazaki | G03G 9/0819 |
| | | | | 430/110.3 |
| 2008/0038559 | A1 | 2/2008 | True | |
| 2008/0072609 | A1* | 3/2008 | Ikeuchi | F25J 1/0015 |
| | | | | 62/54.1 |
| 2009/0293643 | A1 | 12/2009 | Powell et al. | |
| 2009/0314698 | A1* | 12/2009 | Higbee | B01F 27/113 |
| | | | | 210/150 |
| 2011/0098201 | A1 | 4/2011 | Seul et al. | |
| 2011/0152127 | A1 | 6/2011 | Ho | |
| 2011/0159578 | A1 | 6/2011 | Godsey et al. | |
| 2013/0140218 | A1* | 6/2013 | Dobby | B03D 1/1412 |
| | | | | 209/164 |
| 2017/0219945 | A1* | 8/2017 | Matsui | G03G 9/083 |
| 2017/0362159 | A1* | 12/2017 | Liao | C07C 51/43 |
| 2020/0164322 | A1 | 5/2020 | Renick et al. | |
| 2020/0183296 | A1* | 6/2020 | Nishikawa | G03G 9/0836 |

OTHER PUBLICATIONS

International Search Report and Written Opinion issued in International Application No. PCT/US2022/052375 dated Apr. 14, 2023.
International Search Report and Written Opinion issued in International Application No. PCT/US2022/052376 dated May 19, 2023.
International Search Report and Written Opinion issued in International Application No. PCT/US2022/052377 dated May 19, 2023.

* cited by examiner

216

212

214

210

314

402

404

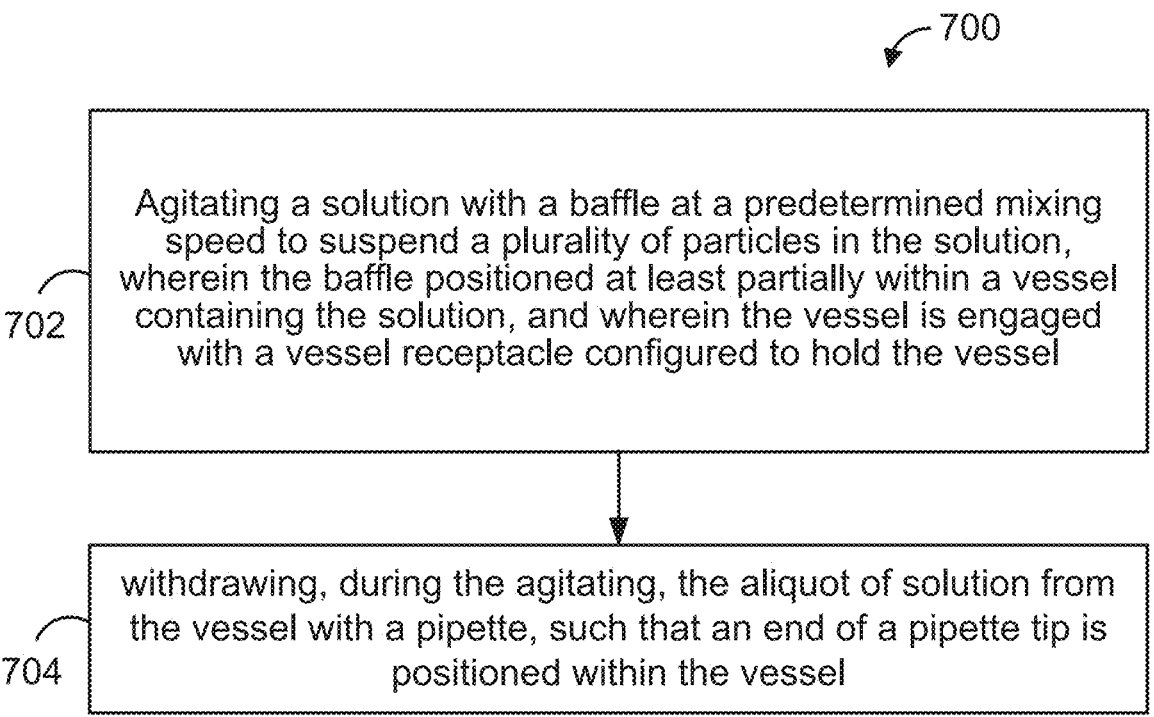

700

702 | Agitating a solution with a baffle at a predetermined mixing speed to suspend a plurality of particles in the solution, wherein the baffle positioned at least partially within a vessel containing the solution, and wherein the vessel is engaged with a vessel receptacle configured to hold the vessel 704 | withdrawing, during the agitating, the aliquot of solution from the vessel with a pipette, such that an end of a pipette tip is positioned within the vessel

Figure 7

DEVICES AND METHODS FOR PARTICLE SOLUTION PREPARATION

CROSS-REFERENCE TO RELATED APPLICATIONS

This application claims priority to U.S. Provisional Patent Application No. 63/288,386, filed on Dec. 10, 2021, U.S. Provisional Patent Application No. 63/288,408, filed on Dec. 10, 2021, U.S. Provisional Patent Application No. 63/288,397, filed on Dec. 10, 2021, and U.S. Provisional Patent Application No. 63/288,378, filed on Dec. 10, 2021, each of which is hereby incorporated by reference in its entirety. Additionally, this application hereby incorporates by reference the following U.S. Patent Applications, each filed on the same date as the present application: U.S. patent application Ser. No. 18/078,510, titled "Devices and Methods for Pipette Alignment", U.S. patent application Ser. No. 18/078,519, titled "Devices and Methods for Particle Solution Testing" and U.S. patent application Ser. No. 18/078, 531, titled "Devices and Methods for Particle Mixing".

FIELD OF THE DISCLOSURE

The present disclosure involves systems and methods for preparing an aliquot of solution containing particles utilizing a baffle inserted into a vessel containing the solution. Namely, devices and methods of the disclosure agitate the solution inside the vessel using a baffle and position an end of a pipette tip at a predetermined depth inside the vessel to withdraw a solution during agitation.

BACKGROUND

Assays (including immunoassays) can be conducted utilizing a variety of different solutions, including solutions containing particles to assist in performing the assays.

SUMMARY

In some examples, particles such as paramagnetic beads, polystyrene particles, or the like, can be suspended within a solution that can be withdrawn with a pipette for testing and identification of components in a sample. In some configurations, different particles may be configured to detect different antibodies, antigens, proteins, or the like. By detecting different, antibodies, antigens, proteins, or the like, the particles can be utilized to perform multiple simultaneous assays on a single sample. To increase the accuracy of assay test results, it is desirable to prepare the same number and homogeneity of particles for each withdrawing event and, prior to withdrawing, ensure that the particles are dispersed evenly throughout the solution.

When operators manually prepare the solution, the homogeneity and number of particles throughout the prepared solution may be inconsistent. For example, if an operator manually prepares the solution containing particles by manually stirring the solution a stir bar inserted into the solution, the rate, depth, and timing of the operator's stirring the solution can significantly affect the type, number, and consistency of particles dispersed throughout (and eventually withdrawn from) the solution. Further, if the operator allows too much time to elapse between manually stirring the solution and withdrawing a sample therefrom, the particles may become less homogenized throughout the solution (e.g., by settling to the bottom of the vessel, clumping together or both, among other potential issues), which in turn can also impact the accuracy and precision of any assay results for which the particles may be used. For example, in some configurations different particles within the solution are utilized to perform different assays. As the homogeneity of the particles within the solution decreases, the likelihood of withdrawing an uneven distribution of the different particles increases, such that particles associated with a specific assay may be over or under represented in a volume of solution withdrawn, which can impact the result of the specific assay. Accordingly, manual preparations of the solution are subject to variability between preparations and/or operators and, thus, can degrade the accuracy and precision of associated assay results.

In an example, a method is described for preparing an aliquot of solution comprising a plurality of particles. The method comprises agitating the solution with a baffle at a predetermined mixing speed to suspend the plurality of particles in the solution, wherein the baffle positioned at least partially within a vessel containing the solution, and wherein the vessel is engaged with a vessel receptacle configured to hold the vessel. The method also comprises withdrawing, during the agitating, the aliquot of solution from the vessel with a pipette, such that an end of a pipette tip is positioned within the vessel.

In another example, a non-transitory computer-readable medium is described, having stored thereon program instructions that, upon execution by a controller cause a controller to perform a set of operations. The set of operations comprises agitating a solution with a baffle at a predetermined mixing speed to suspend a plurality of particles in the solution, wherein the baffle positioned at least partially within a vessel containing the solution, and wherein the vessel is engaged with a vessel receptacle configured to hold the vessel. The set of operations also comprises withdrawing, during the agitating, the aliquot of solution from the vessel with a pipette, such that an end of a pipette tip is positioned within the vessel.

The features, functions, and advantages that have been discussed can be achieved independently in various examples or may be combined in yet other examples. Further details of the examples can be seen with reference to the following description and drawings.

BRIEF DESCRIPTION OF THE FIGURES

The above, as well as additional features will be better understood through the following illustrative and non-limiting detailed description of example embodiments, with reference to the appended drawings.

FIG. 7 illustrates a method, according to an example embodiment.

Figure 1:
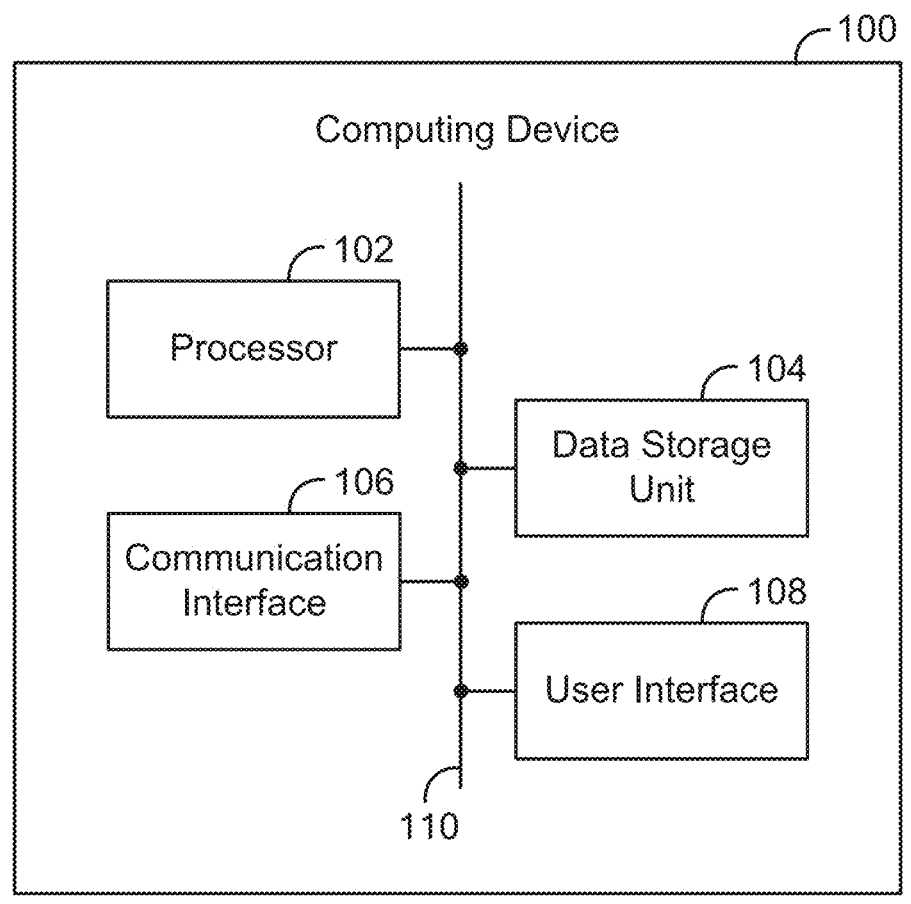
FIG. 1 illustrates a simplified block diagram of an example computing device, according to an example embodiment.

All the figures are schematic, not necessarily to scale, and generally only show parts which are necessary to elucidate example embodiments, wherein other parts may be omitted or merely suggested.

DETAILED DESCRIPTION

Example embodiments will now be described more fully hereinafter with reference to the accompanying drawings. That which is encompassed by the claims may, however, be embodied in many different forms and should not be construed as limited to the embodiments set forth herein; rather, these embodiments are provided by way of example. Furthermore, like numbers refer to the same or similar elements or components throughout.

Within examples, the disclosure is directed to devices and methods for preparing and withdrawing samples of a solution containing one or types of particles utilizing a baffle. In particular, as described in the example embodiments, the one or more types of particles may include one or more of the following: microbeads, microparticles, micropellets, microwafers, paramagnetic beads, microparticles, paramagnetic microparticles, or the like. In embodiments, each of the particles may include an identifying feature, such as a bar code, a nickel bar code, and/or identifying features other than bar codes, including a color, a shape, an alphanumeric symbol, and/or the like. Moreover, the particles may be magnetic or paramagnetic. Particles suitable for use in the disclosure are capable of attachment to other substances such as derivatives, linker molecules, proteins, nucleic acids, or combinations thereof. The capability of the particles to be attached to other substances can result from the particle material as well as from any further surface modifications or functionalization of the particle. The particles can be functionalized or be capable of becoming functionalized in order to covalently or non-covalently attach proteins, nucleic acids, linker molecules or derivatives as described herein. For example, the surface of the particle can be modified or functionalized with amine, biotin, streptavidin, avidin, protein A, sulfhydryl, hydroxyl and carboxyl. Particles may be spherical or other shapes, may be light transmissive and may be digitally coded such as for example, by an image that provides for high contrast and high signal-to-noise optical detection to facilitate identification of the bead. To the extent an image is present, the image may be implemented by a physical structure having a pattern that is partially substantially transmissive (e.g., transparent, translucent, and/or pervious to light), and partially substantially opaque (e.g., reflective and/or absorptive to light) to light. The pattern of transmitted light is determined (e.g., by scanning or imaging), and the code represented by the image on the coded bead can be decoded. Various code patterns, such as circular, square, or other geometrical shapes, can be designed as long as they can be recognized by an optical decoder. Examples of these one or more types of particles may be found at: U.S. Pat. Nos. 7,745,091, 8,148,139, and 8,614,852.

Additionally or alternatively, the one or more types of particles may comprise one or more materials, including one or more of the following: glass, polymers, polystyrene, latex, elemental metals, ceramics, metal composites, metal alloys, silicon, or of other support materials such as agarose, ceramics, glass, quartz, polyacrylamides, polymethyl methacrylates, carboxylate modified latex, melamine, and Sepharose, and/or one or more hybrids thereof. In particular, useful commercially available materials include carboxylate modified latex, cyanogen bromide activated Sepharose beads, fused silica particles, isothiocyanate glass, polystyrene, and carboxylate monodisperse microspheres. Furthermore, the one or more types of particles may also comprise one or more specific shapes, dimensions, and/or configurations and may be modified for one or more specific uses. For example, the particles may be a variety of sizes from about 0.1 microns to about 100 microns, for example about 0.1, 0.5, 1.0, 5, 10, 20, 30, 40 50, 60, 70, 80 90 or 100 microns. For example, the one or more types of particles may be surface modified and/or functionalized with biomolecules for use in biochemical analysis.

The particles of the disclosure may be used in various homogenous, sandwich, competitive, or non-competitive assay formats to generate a signal that is related to the presence or amount of an analyte in a test sample. The term "analyte," as used herein, generally refers to the substance, or set of substances in a sample that are detected and/or measured, either directly or indirectly. In various aspects the assays of the disclosure, examples include sandwich immunoassays that capture an analyte in a sample between a binding member (e.g., antibody) attached to the particle and a second binding member for the analyte that is associated with a label. In another example embodiment, the binding member on the particle may be an antigen (e.g., protein) that binds an antibody of interest in a patient sample in order to capture the antibody on the particle. The presence of the antibody can then be detected with a label conjugated to a second binding member specific for an antibody. The second binding member attached to the label may be the antigen conjugated to the label or the binding member may itself be an antibody (e.g., anti-species antibody) that is conjugated the label. In example embodiments, these characteristics may be referred to herein as a "unique identifying feature"

of the particle. Other examples are possible. For example, the particle may also bind to a fluorescent tag or label, which may present a "unique identifying feature" of the particle to which the fluorescent tag or label might bind under a fluorescent lighting.

In another example embodiment, the assay methods of the disclosure are competitive immunoassays for detection of antibody in the sample. A competitive immunoassay may be carried out in the following illustrative manner. A sample, from an animal's body fluid, potentially containing an antibody of interest that is specific for an antigen, is contacted with the antigen attached to the particle and with the anti-antigen antibody conjugated to a detectable label. The antibody of interest, present in the sample, competes with the antibody conjugated to a detectable label for binding with the antigen attached to the particles. The amount of the label associated with the particles can then be determined after separating unbound antibody and the label. The signal obtained is inversely related to the amount of antibody of interest present in the sample.

In an alternative example embodiment of a competitive a sample, an animal's body fluid, potentially containing an analyte, is contacted with the analyte conjugated to a detectable label and with an anti-analyte antibody attached to the particle. The antigen in the sample competes with analyte conjugated to the label for binding to the antibody attached the particle. The amount of the label associated with the particles can then be determined after separating unbound antigen and label. The signal obtained is inversely related to the amount of analyte present in the sample.

Antibodies, antigens, and other binding members may be attached to the particle or to the label directly via covalent binding with or without a linker or may be attached through a separate pair of binding members as is well known (e.g., biotin: streptavidin, digoxigenin: anti-digoxiginen).

Assays using these solutions are often conducted over a series of agitation events and withdrawing events. In practice, the particles in the solution may bind together (often referred to as "clumping") or bind and/or settle on the bottom or sides of a vessel in which the solution is prepared. This binding may result in an inconsistent dispersion of the particles in the solution. For example, in some instances the density of the particles may be lower than the density of the solution, which may result in the particles floating to the top of the solution and inconsistent particle dispersion throughout the solution. Alternatively, the density of the particles may be higher than the density of the solution, which may result in the particles sinking to the bottom of the solution, which may result in clumping at the bottom and/or inconsistent particle dispersion throughout the solution When these particles clump together, they may not be accurately identified or accounted for in an assay in which the solution containing the particles may be used. In another example, in instances where the particles bind/settle on the bottom or sides of the vessel in which the solution containing the particles is prepared, the particles may remain in the vessel as solution is pipetted out of the vessel. To help address this issue, a vessel with an insertable baffle, which is engaged with a vessel receptacle and coupled to a mixer controlled via a programmable controller, can agitate the solution (for example by way of rotating the vessel receptacle and the vessel) before a withdrawing event to more consistently disperse the particles in the prepared solution. However, the mixing speed and mixing pattern of the mixer, the engagement of the vessel and the vessel receptacle, and the position, configuration, and relative motion of the insertable baffle in relation to the vessel and the solution during an agitation and/or withdrawing event may affect the consistency of the assay results and/or the type and consistency of particles dispersed within the solution.

To help address these issues, a program for controlling the mixer can be utilized to cause the mixer to perform a preset series of agitation events to improve consistency of the solution in the vessel, thereby increasing the accuracy of the assay results as compared to assays performed with inconsistent types or numbers of particles. Namely, the controller of the mixer can cause the vessel receptacle, vessel, and/or the baffle to execute a series of agitation events where the mixing speed of the mixer is set to a predetermined rotational velocity, pattern (e.g., clockwise rotation, counterclockwise rotation, alternating clockwise/counterclockwise rotations, etc.), and/or other parameters. For example, the controller of the mixer may cause the vessel receptacle, vessel, and/or the baffle to move in a pattern and/or specific tolerance to ensure that one or more components operate within a specific range of parameters in relation to one another. For example, the controller may cause the mixer to rotate the vessel receptacle (and the vessel and baffle engaged with the vessel receptacle) to rotate in an alternating clockwise/counterclockwise rotational pattern such that the solution in the vessel is stirred in alternating directions within a predetermined tolerance and/or rotational velocity (e.g., a velocity sufficient to thoroughly disperse the particles throughout the solution).

In this manner, in example embodiments, certain mixing speeds and patterns may more consistently agitate the solution, which can lead to consistent dispersion of the particles within the solution, thereby producing more accurate and consistent particle counts than other mixing speeds and patterns.

Additionally, the controller can cause one or more pipettes inserted into the solution to agitate and/or withdraw solution at a predetermined depth within the vessel and with respect to the depth of the solution within the vessel and may do so while the mixer is causing the vessel receptacle, vessel, and/or the baffle to execute a series of agitation events. In example embodiments, the controller may cause the pipettes to agitate and/or withdraw solution at a predetermined depth within the vessel and with respect to the depth of the solution within the vessel by controlling one or more components of the systems and devices described here (e.g., the pipettes, the mixer, etc.) and/or one subparts thereof (e.g., one or more motors, actuators, and/or other mechanical components of the mixer, the pipettes, etc.). In these embodiments, the accuracy of particle count and/or type of particles withdrawn from solution may be improved as compared to systems that do not cause the pipettes to agitate and withdraw solution at a predetermined depth, including during a series of agitation events by the mixer, the vessel receptacle, vessel, and/or the baffle. For example, positioning the end of the pipette tip at or near the center or middle of the volume (e.g., the center line of the height of the solution in the vessel or the "vertical center") may allow the pipette to more effectively withdraw the solution to produce more consistent particle counts compared to other positions such as the bottom of the solution or the top of the solution. As such, in example embodiments, the controller causes the pipettes to be positioned such that, during a withdrawing event, the end of the pipette tip is at or near the vertical and/or horizontal center of the volume of the solution or another position that is consistent, on a relative volume basis, for withdrawn from the vessel, including during a series of agitation events by the mixer, the vessel receptacle, vessel, and/or the baffle.

Similarly, positioning the end of the pipette tip at or near the center or middle of the horizontal cross section of the vessel (the "horizontal center") may allow the pipette to more consistently agitate the solution and/or withdrawn more consistent samples of the solution during solution agitation events involving the mixer, the vessel receptacle, vessel, and/or the baffle. As used in this disclosure, horizontal indicates a direction transverse to the vertical direction, and extending outward from a vertical centerline of the referenced body (e.g., the horizontal center of a vessel stabilized in one position in a vessel receptacle). This specific positioning can produce more accurate and consistent particle counts compared to other positions, such as the side of the vessel.

In practice, removal of the contents of a vessel may be performed over a series of withdrawing events. For example, a first volume of the solution may be withdrawn, and a first assay sample prepared (e.g., by pipetting an aliquot of the prepared solution into one or more vials for use in an assay or assays on a sample). Then a second volume of the solution may be withdrawn, and a second assay sample prepared. This process may be repeated a number of times (e.g., 12). As noted above, during each of the withdrawing events it may be beneficial for the withdrawing tip of the pipette to be at or near the vertical and/or horizontal center of the solution. However, as the volume of solution is reduced with each withdrawing event, the vertical center of the solution becomes lower within the vessel. Thus, attaining consistent vertical positioning of the pipette within the solution as the volume decreases may also provide more consistent assay results (e.g., by improving the consistency of the amount and/or type of particles withdrawn at each withdrawing event over the series of withdrawing events), particularly during solution agitation events involving the mixer, the vessel receptacle, vessel, and/or the baffle. Further, these agitation and withdrawing events may be performed across multiple vessels of solution at once.

Devices and methods of the present disclosure also involve positioning a pipette such that the end of the pipette tip is at or near the vertical and/or horizontal center of the solution or another consistent location (e.g., 30%, 40%, 50%, 60% or 70% of the height of the solution) during each withdrawing event in a series of withdrawing events. While the vertical center of the vessel is typically appropriate for most series of withdrawing events, another position with the solution for each withdrawing event may also be appropriate depending on the amount of solution and the type of particles within the vessels. Additionally, one or more other factors may influence the proper withdrawing position, including one or more parameters that may be adjusted during solution agitation events (e.g., mixer speed, the position of the vessel receptacle and/or vessel, and/or the baffle configuration).

Indeed, in some embodiments, the position of the pipette tip may be adjusted with each withdrawing event in order to accommodate the amounts of solutions and the particles. For instance, as the solution depth diminishes, the vertical center may be too close to the bottom of the vessel in order to provide a withdrawal of solution with number of particles that is consistent with the particles from a previous withdrawing event. For example, as the vertical center becomes too close to the bottom of the vessel, the particles may cling to the bottom of the vessel and/or settle at the bottom of the vessel due to one or more factors (e.g., gravity), the withdrawing position may be adjusted to compensate and provide a more homogeneous solution withdrawing evert. For example, once the vertical center becomes too close to the bottom of the vessel, the withdrawing position may be adjusted to withdraw at a distance that is great than the vertical center of the remaining solution (e.g. to withdraw a solution that is less concentrated with particles as compared to the solution at the vertical center), particularly in light of one or more parameters that may be adjusted during solution agitation events (e.g., mixer speed, the position of the vessel receptacle and/or vessel, and/or the baffle configuration).

In some embodiments, a vessel receptacle configured to detachably associate with the mixer can be utilized to secure and stabilize the vessel. Additionally, the vessel receptacle can be utilized to align and/or secure the vessel containing the solution in relation to one or more other components of the methods, devices, and systems described herein, including the insertable baffle, the pipettes, and/or other components that contribute to the preparation and/or the withdrawal of the solution for assay testing. In particular, the vessel receptacle secures and stabilizes the vessel and an associated baffle during agitation and withdrawing events, so that solution and particle agitation and/or position are consistent during the withdrawing events (e.g., from withdrawing event to withdrawing event and/or operator to operator) using the same vessels over multiple solution preparation and/or using different vessels and/or samples in different vessels. In example embodiments, multiple vessel receptacles may integrate with and be interchangeable in relation to the mixer, so that multiple vessels may be used in solution preparation in a consistent, repeatable, and efficient manner (e.g., by using one or more quick connections that are standardized over a variety of vessel receptacles and consistently integrate the vessel receptacle, the vessel, and the baffle with the mixer).

Referring now to the figures, FIG. 1 is a simplified block diagram of an example computing device 100 of a system (e.g., those illustrated in FIGS. 2A-2B, described in further detail below). Computing device 100 can perform various acts and/or functions, such as those described in this disclosure. Computing device 100 can include various components, such as processor 102, data storage unit 104, communication interface 106, and/or user interface 108. These components can be connected to each other (or to another device, system, or other entity) via connection mechanism 110.

Processor 102 can include a general-purpose processor (e.g., a microprocessor) and/or a special-purpose processor (e.g., a digital signal processor (DSP)).

Data storage unit 104 can include one or more volatile, non-volatile, removable, and/or non-removable storage components, such as magnetic, optical, or flash storage, and/or can be integrated in whole or in part with processor 102. Further, data storage unit 104 can take the form of a non-transitory computer-readable storage medium, having stored thereon program instructions (e.g., compiled or non-compiled program logic and/or machine code) that, when executed by processor 102, cause computing device 100 to perform one or more acts and/or functions, such as those described in this disclosure. As such, computing device 100 can be configured to perform one or more acts and/or functions, such as those described in this disclosure. Such program instructions can define and/or be part of a discrete software application. In some instances, computing device 100 can execute program instructions in response to receiving an input, such as from communication interface 106 and/or user interface 108. Data storage unit 104 can also store other types of data, such as those types described in this disclosure.

Communication interface 106 can allow computing device 100 to connect to and/or communicate with another other entity according to one or more protocols. In one example, communication interface 106 can be a wired interface, such as an Ethernet interface or a high-definition serial-digital-interface (HD-SDI). In another example, communication interface 106 can be a wireless interface, such as a cellular or WI FI interface. In this disclosure, a connection can be a direct connection or an indirect connection, the latter being a connection that passes through and/or traverses one or more entities, such as such as a router, switcher, or other network device. Likewise, in this disclosure, a transmission can be a direct transmission or an indirect transmission.

User interface 108 can facilitate interaction between computing device 100 and a user of computing device 100, if applicable. As such, user interface 108 can include input components such as a keyboard, a keypad, a mouse, a touch sensitive panel, a microphone, a camera, and/or a movement sensor, all of which can be used to obtain data indicative of an environment of computing device 100, and/or output components such as a display device (which, for example, can be combined with a touch sensitive panel), a sound speaker, and/or a haptic feedback system. More generally, user interface 108 can include hardware and/or software components that facilitate interaction between computing device 100 and the user of the computing device 100.

Computing device 100 can take various forms, such as a workstation terminal, a desktop computer, a laptop, a tablet, a mobile phone, or a controller.

Now referring to FIGS. 2A-2E, a solution preparation system 200 is illustrated and includes a vessel 202, a vessel opening 204, a vessel receptacle 206, a vessel receptacle adjustment mechanism 208, a vessel receptacle alignment tab 210, a vessel receptacle quick connector opening 212, a mixer 214, and a vessel receptacle quick connector 216, a baffle 218, a baffle connector 220, baffle arms 222, a baffle opening 224, one or more pipettes 226, are depicted, according to an example embodiment.

In examples, the vessel receptacle 206 is configured to hold a vessel 202, which may be interchanged with one or more additional vessels (e.g., by loosening vessel receptacle adjustment mechanism 208). In some examples, the vessel receptacle 206 is configured to hold a variety of vessels, some or all of which may meet Society for Biomolecular Screening ("SBS") standards or other industry standard for laboratory equipment. In the embodiment shown in FIGS. 2A-2E, the vessel receptacle 206 secures and positions vessel 202 such that when the vessel receptacle 206 rotates, the vessel 202 would rotate as well, thereby agitating the solution contained in the vessel 202.

Additionally, vessel receptacle 206 may align the vessel such one or more particularly configured pipettes (e.g., one or more SBS standard pipettes) can be inserted and take withdrawals from the vessel 202. Additionally, although various components of the systems and/or methods described herein may refer to SBS-compliment components, they are described for the purposes of illustrating example embodiments and other, additional components may be utilized.

Figure 2A:
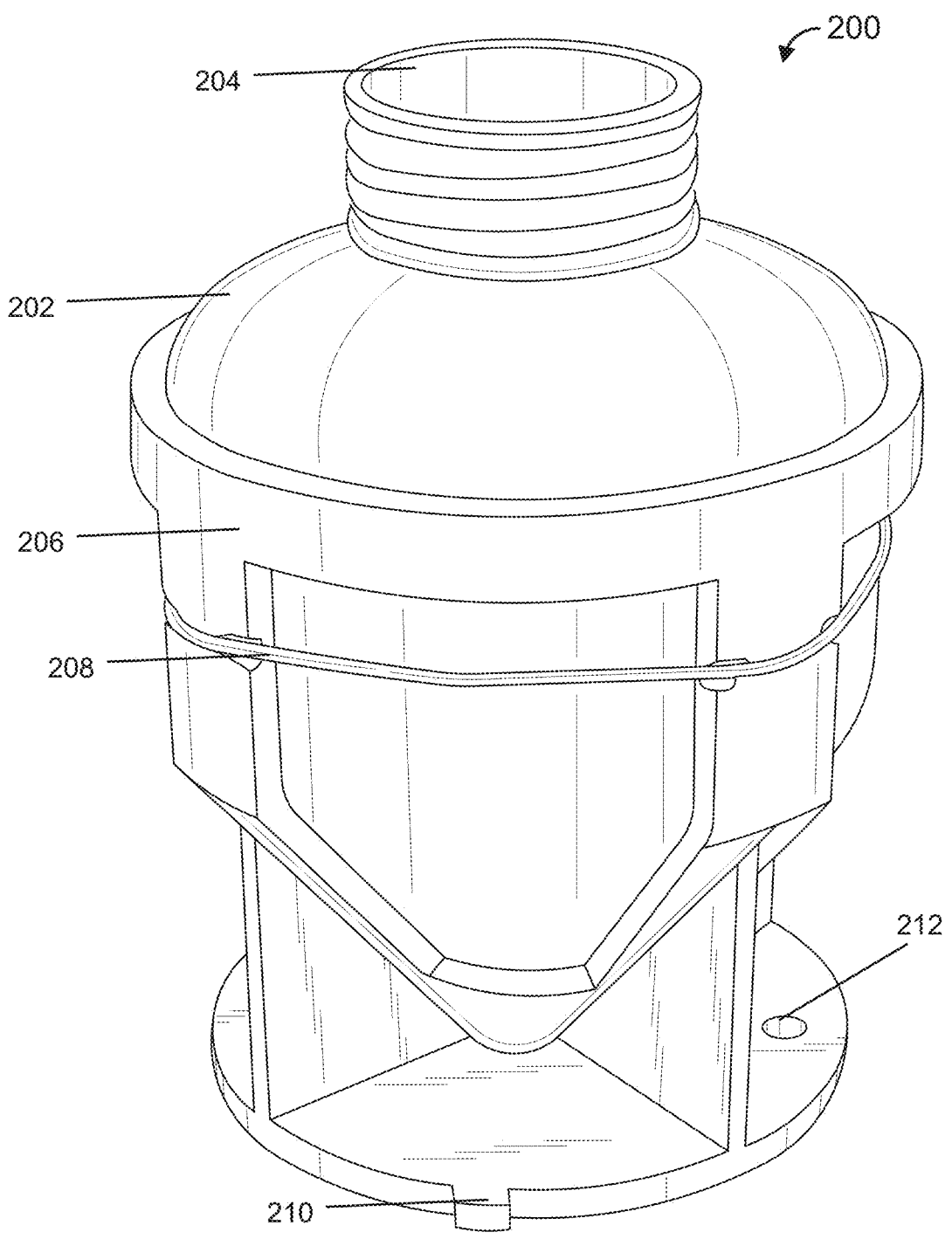
FIG. 2A illustrates a vessel and vessel receptacle, according to an example embodiment.

For example, although the vessel receptacle 206 is illustrated in FIGS. 2A-2E as holding one vessel in one direction relative the mixer, baffle, and/or one or more pipettes, vessel receptacle 206 may be implemented in one or more additional or alternative configurations. For example, although vessel receptacle 206 is illustrated in FIG. 2A to hold a specific shape and circumference vessel, it should be apparent to one of skill in the art that the vessel receptacle 206 could be adjustable in one or more manners (e.g., to accommodate vessels of different circumferences and/or shapes). For example, vessel receptacle 206 may have more or less structural support for its walls in one or more other directions (e.g., in the space between the four portions that extend upward from the base of the vessel receptacle) to improve structural strength and ability to secure the vessel and/or may be implemented in various proportions compared to the embodiments illustrated in FIGS. 2A-2E. For example, the vessel receptacle 206 may be taller or shorter than the embodiments illustrated in FIGS. 2A-2E (e.g., to improve the rigidity and/or grip of the vessel receptacle 206 on the vessel inserted therein).

In some embodiments the vessel receptacle 206 may incorporate one or more additional materials to provide additional functionality. For example, vessel receptacle 206 may be lined with a rubber and/or foam that might allow the vessel to more securely seat in the vessel receptacle 206 as compared to vessel receptacle 206 that do not include a liner. Additionally, these materials lining the vessel receptacle 206 may absorb one or more mechanical actions of the mixer, vessel, baffle, or other components, thereby reducing transfer of mechanical energy to the vessel during withdrawing events. In some embodiments, the vessel 202 may be molded into the vessel receptacle 206.

In some examples, the vessel receptacle 206 may be adjustable to hold different sizes, numbers, or types of vessel. For example, although the vessel receptacle 206 is shown in FIG. 2A as semi-circular shape with a vessel opening 204 at one end and terminating into a point at the other end with vessel receptacle walls that contour to the specifically shaped vessel illustrated in FIG. 2A, the vessel receptacle 206 may take a different shape (e.g., oval, square) and/or be made with walls in one or more other configurations. For example, vessel receptacle 206 may be configured to make contact with the vessel around only the widest horizontal portion of the vessel (e.g., a band around the widest horizontal portion of the vessel) and not contour to the specifically shaped vessel illustrated in FIG. 2A.

Additionally or alternatively, the height of the vessel receptacle 206 (or individual components thereof) may be adjustable to accommodate different types of pipettes and/or pipette tips. In some examples, the height of the vessel receptacle 206 may also be adjusted to position the end of the pipette tip at one or more predetermined depths during a withdrawing event. In example embodiments, the height of the vessel receptacle 206 may be adjustable to accommodate different types of pipettes and/or pipette tips and/or further stabilize the vessel during withdrawing events. In practice, the vessel receptacle 206 works to stabilize vessel 202 during agitation and withdrawing of the particle solution. Stabilization of the vessel 202 is desirable during withdrawing and agitation of a particle solution to reduce variability among operators by reducing inconsistencies between particle counts over a series of withdrawing events. In some examples, these particles may be microbeads, microparticles, micropellets, microwafers, paramagnetic beads, microparticles, paramagnetic microparticles, or the like. In embodiments, the particles contain one or more identifying features such as a bar code, a nickel bar code, an alphanumeric symbol, a color, a shape, or some combination of thereof, among other possibilities. Particle sizes may range from about 70×25×6 micrometers ($\mu$m) to about 80×30×6 $\mu$m and must be able to be withdrawn into the pipette tip. In embodiments, the vessel receptacle 206 is positioned to axially align the vessel 202 and other components of the solution preparation system 200 prior to solution agitation and withdrawing events.

Figure 2B:
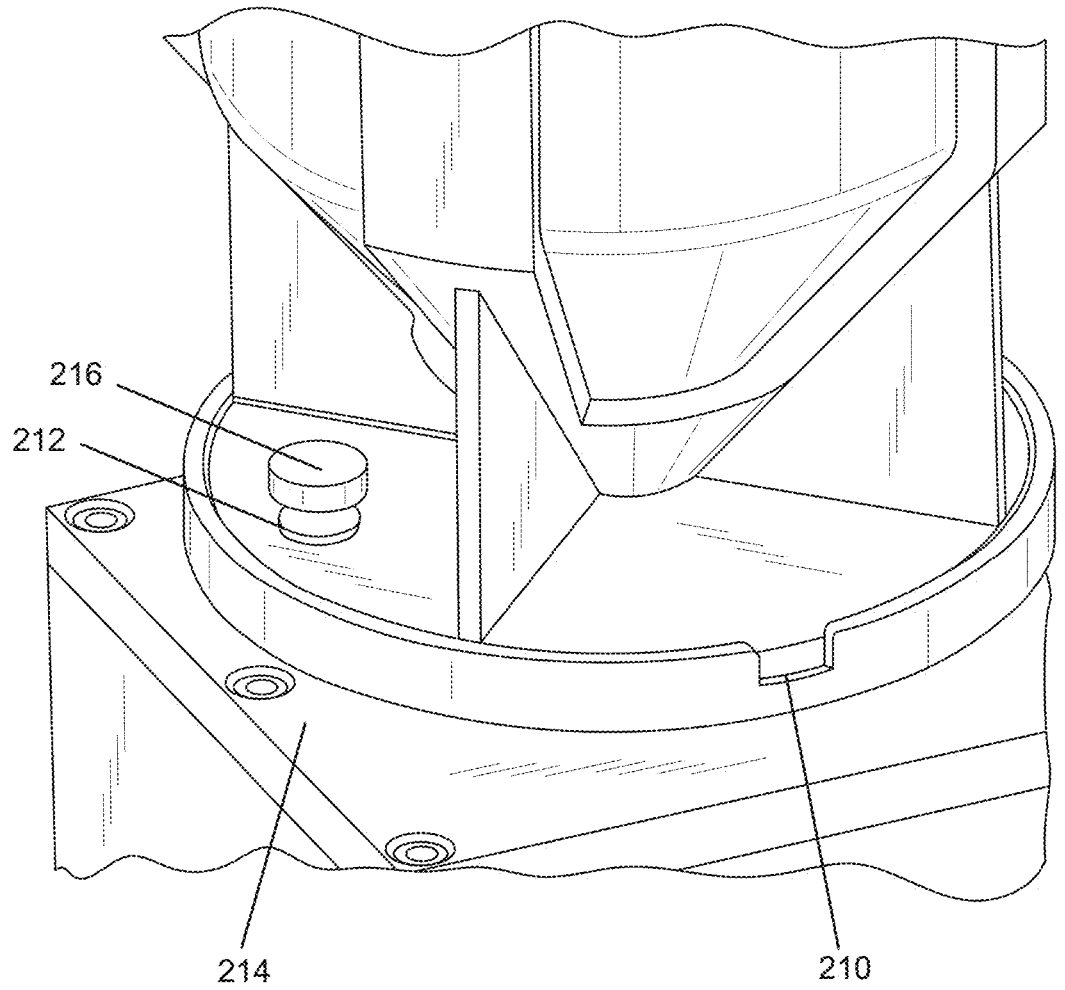
FIG. 2B illustrates an enlarged view of the vessel and vessel receptacle of FIG. 2A, according to an example embodiment.

Turning to FIG. 2B, the base of vessel receptacle 206 may be configured to detachably associate from a mixer 214, such as the one illustrated in FIG. 2B. For example, the dimensions of the base of vessel receptacle 206 can be the same or substantially similar to those of the dimensions of a mounting plate of the mixer 214, which may be connected to one or more motors of the mixer 214 and actuate/rotate in relation to the mixer.

In some examples, vessel receptacle 206 may include receptacle fastening mechanisms to detachably associate with the mixer 214 by way of a mixer fastening mechanism, such as a screw or other threaded connection in a manner that is not destructive to the vessel receptacle 206, the vessel 202, the mixer 214, the baffle 218, the pipettes 226, and/or other components of the illustrated devices. In some examples, as illustrated in FIG. 2B, a vessel receptacle alignment tab 210 integrates with a recess in the mounting plate of mixer 214. The alignment tab 210 may orient the vessel receptacle in one or more directions relative to the mixer 214 and may also provide further structural support for the vessel receptacle 206 in relation to the mixer. The alignment tab 210 may also provide feedback and confirmation to the user of the vessel receptacle 206 and/or the mixer 214 that vessel receptacle 206 is properly mounted to the mixer 214 and is ready for an agitation event using the vessel receptacle 206 and/or the mixer 214.

In some examples, as illustrated in FIG. 2B, a vessel receptacle quick connector opening 212 integrates with a vessel receptacle quick connector 216 and mounts the vessel receptacle 206 on the mixer 214 (e.g., via a mounting plate of mixer 214). In some examples, the vessel receptacle quick connector 216 can include screws and/or a threaded connection compatible with the mixer 214 to keep the vessel receptacle 206 in place during agitation and withdrawing events. In this regard, vessel receptacle 206 may be permanently or detachably associated with the mixer 214.

The vessel receptacle quick connector 216 may orient the vessel receptacle in one or more directions relative to the mixer 214 and may also provide further structural support for the vessel receptacle 206 in relation to the mixer. The vessel receptacle quick connector 216 may also provide feedback and confirmation to the user of the vessel receptacle 206 and/or the mixer 214 that vessel receptacle 206 is properly mounted to the mixer 214 and is ready for an agitation event using the vessel receptacle 206 and/or the mixer 214. Additionally, the alignment tab 210 and/or the vessel receptacle quick connector 216 may allow the user to quickly, consistently, and securely change vessel receptacles for a variety of vessels, solutions, and/or mixing protocols be implemented in connection with the mixer 214.

In a further aspect, in practice, the vessel receptacle 206 may be configured to be permanently or removably mounted to the mixer 214 in order to support a pipette in a manner that consistently and repeatedly positions the vessel receptacle 206 (and vessels therein) in relation to the pipette. In this manner, the withdrawing events associated with the vessel receptacle, vessel, and pipettes may be consistently and repeatedly performed, thereby improving the results of solution preparation and any assays and other testing results associated therewith.

Figure 2C:
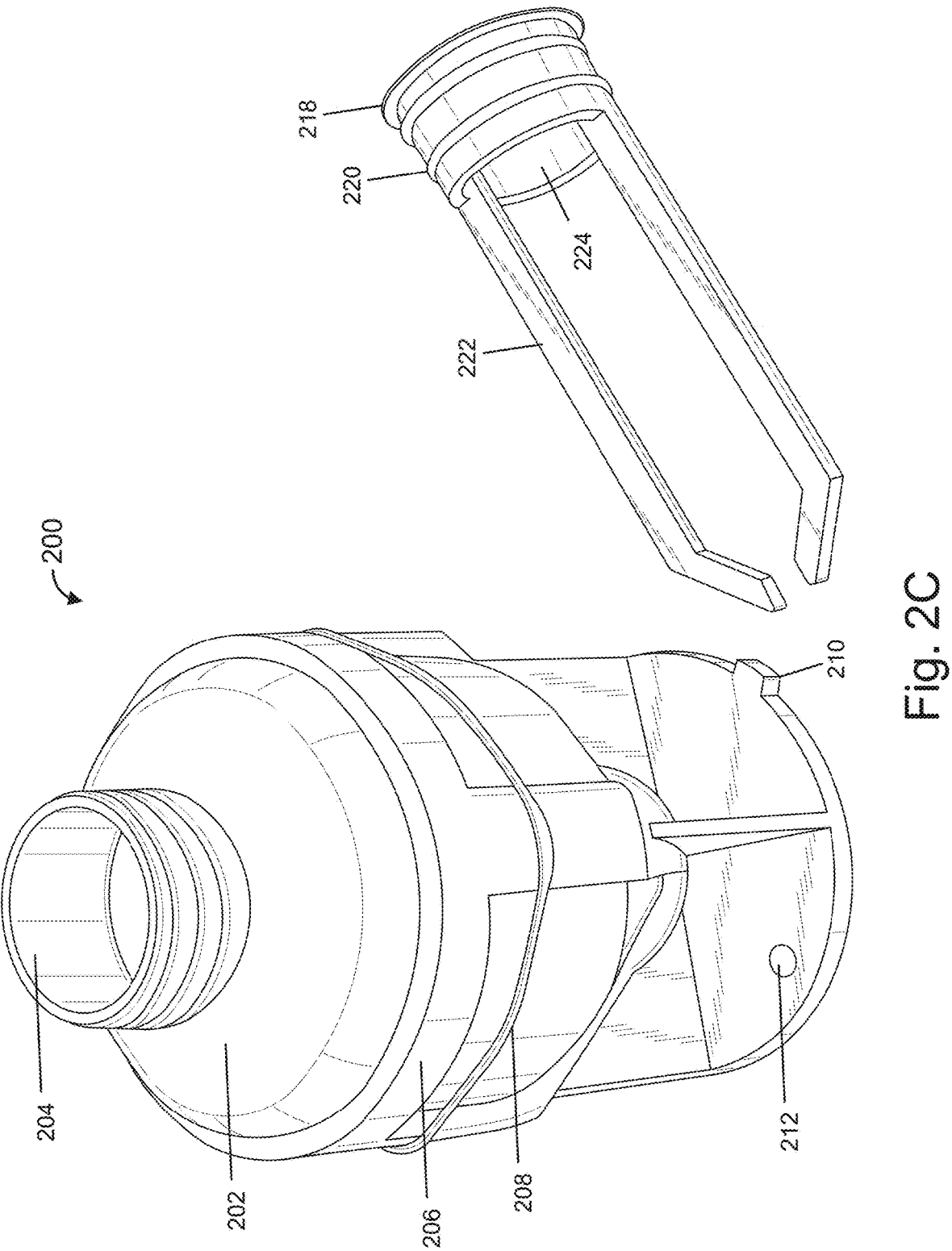
FIG. 2C illustrates the vessel and the vessel receptacle of FIGS. 2A and 2B and a baffle, according to an example embodiment.

Turning to FIG. 2C, vessel receptacle 206 may also integrate with a baffle 218 that may be inserted into vessel 202 via vessel opening 204. In an example, the vessel 202 may define the vessel opening 204 according to a specific circumference, which may be approximate to a circumference of the baffle 218. Additionally or alternatively, in an example embodiment, upon inserting the baffle 218 into the vessel 202 via vessel opening 204, the baffle connector 220 of the baffle 218 may secure the baffle 218 in the vessel 202 by making contact with the inner walls of vessel opening 204. Further, although the baffle connector 220 is illustrated in FIG. 2C as two resilient rings positioned at the top portion of baffle 218 in FIG. 2C, the baffle connector 220 may be configured in additional or alternative manners, including by adding or removing baffle connectors 220 and/or using different materials for baffle connector 220.

For example, although baffle connector 220 is illustrated in FIG. 2C to integrate into a specific shape and circumference vessel, it should be apparent to one of skill in the art that the baffle connector 220 could be adjustable in one or more manners (e.g., to accommodate vessels of different circumferences and/or shapes). For example, baffle connector 220 may be configured to securely position the baffle 218 in relation to the vessel 202, so that when the vessel 202 is rotated, the baffle 218 rotates directly in proportion to the vessel 202 (i.e., rotates with the vessel 202). In other examples, however, baffle connector 220 may be configured to move the baffle 218 in relation to the vessel 202, so that when the vessel 202 is rotated, the baffle 218 rotates indirectly (or not at all) in proportion to the vessel 202. In examples, the baffle connector 220 may be taller or shorter than the embodiments illustrated in FIGS. 2C-2E (e.g., to improve the rigidity and/or grip of the baffle connector 220 on the vessel in which the baffle is inserted). Other examples are possible.

In examples, baffle connector 220 may be lined with a rubber and/or foam that might allow the baffle to more securely seat in the vessel opening 204 as compared to baffle connector 220 that do not include a liner. Additionally, these materials lining the baffle connector 220 may absorb one or more mechanical actions of the mixer, vessel, baffle, or other components, thereby reducing transfer of mechanical energy to the vessel during withdrawing events. In some embodiments, the baffle 218 may be molded into the vessel 202.

In one aspect, in example embodiments, the baffle 218 has one or more baffle arms 222 that extend into the vessel 202 when the baffle 218 is inserted into vessel 202 via vessel opening 204. In an example, the baffle arms 222 may be shaped to contour the specifically shaped vessel illustrated in FIG. 2C (e.g., straight arms that terminate in an angled portion that maps the contours of the bottom of vessel 202). In example embodiments, the baffle arms 222 may be taller or shorter than the embodiments illustrated in FIGS. 2C-2E (e.g., to adjust the depth of the baffle arms 222 in relation to the vessel in which the baffle is inserted). Additionally, in example embodiments, there may be more or fewer baffle arms 222 than illustrated in FIG. 2C. The baffle 218 and the baffle arms 222 may assist in disrupting the flow of solution within the vessel 202 as the vessel 202 (and baffle 218) rotate, thereby assisting in agitating and distributing particles within the solution.

In example embodiments, the baffle arms 222 may be made of one more materials, depending on the solution into which the baffle arms 222 are to be inserted. For example, baffle arms 222 may be made of one or more non-stick materials so that one or more particles in the solution do not interact with and/or stick to the baffle arms 222 during mixing. Additionally or alternatively, baffle arms 222 may be made of one or more materials that interact with one or more characteristics of the one or more particles in the solution. For example, if the particles are magnetic or paramagnetic, baffle arms 222 may be made of a material that repels the one or more particles (or at least does not interact with the particles, magnetically) in the solution during mixing. Other examples are possible.

In an example embodiment, upon inserting the baffle 218 into the vessel 202 via vessel opening 204, the baffle arms 222 may be directly connected to the baffle 218 and/or baffle connector 220 to secure the baffle arms 222 in the vessel 202 so that when the vessel is rotated, the baffle arms 222 move in the direct rotational pattern of the vessel 202. By doing so, the baffle arms 222 may agitate any solution and/or particles contained in the vessel 202 during agitation. In a further aspect, the baffle arms 222 may be connected to the baffle 218 and/or baffle connector 220 using hardware that allows the baffle arms 222 to be adjusted in relation to the baffle 218 and/or baffle connector 220 (e.g., via set screws allowing the relative angles of the baffle arms 222 to be adjusted and/or removed altogether). In other examples, the baffle arms 222 may be non-detachably coupled to the baffle 218 and/or baffle connector 220 (e.g., via manufacturing the baffle arms 222, the baffle 218, and/or baffle connector 220 as one piece).

In other examples, baffle connector 220, baffle 218, and/or baffle arms 222 may be configured to not move in relation to the vessel 202, so that when the vessel 202 is rotated, the baffle arms 222 rotate indirectly (or not at all) in proportion to the vessel 202. For example, the baffle arms 222 may not be directly connected to the baffle 218 and/or baffle connector 220. For example, there may be a set of ball bearings disposed between the baffle arms 222 and the baffle connector 220 and/or baffle 218 such that when the vessel 202 is rotated, the baffle arms 222 remain stationary (or substantially stationary) in relation to the motion of the vessel 202.

Additionally or alternatively, the baffle 218 may be configured (or adjustable) to accommodate different types of pipettes and/or pipette tips. In some examples, the baffle 218 may define a baffle opening 224 that allows one or more pipettes to be inserted into the vessel 202 while the baffle 218 is integrated into the vessel 202 via vessel opening 204. In example embodiments, baffle opening 224 may be adjustable to accommodate different types of pipettes and/or pipette tips and/or further stabilize the one or more pipettes in relation to the vessel 202 and/or the baffle 218 during withdrawing events.

Figure 2D:
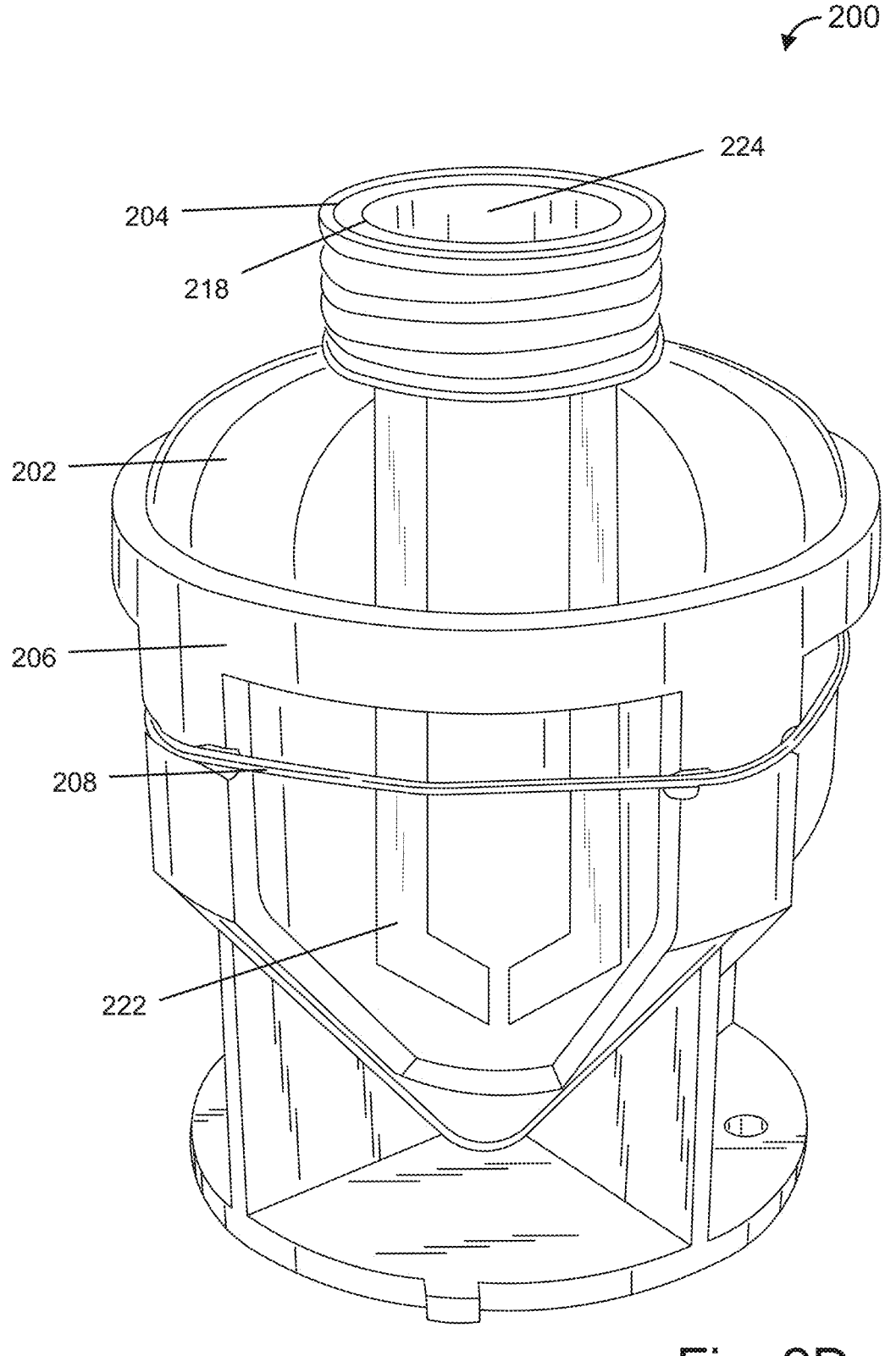
FIG. 2D illustrates the vessel, vessel receptacle, and baffle of FIGS. 2A, 2B, and 2C, and a pipette according to an example embodiment.

Specifically, turning to FIG. 2D, the vessel 202, vessel receptacle 206, and baffle 218 are assembled so that the vessel 202 is integrated with baffle 218. In FIG. 2D, baffle arms 222 extend into the body of the vessel 202 (and thereby into any solution contained in vessel 202). In FIG. 2D, in an example embodiment, the vessel 202 may defines the vessel opening 204 according to a specific circumference, which is approximately the same as the circumference of the baffle 218. As shown in FIG. 2D, in an example embodiment, upon inserting the baffle 218 into the vessel 202 via vessel opening 204, the baffle connector 220 secures the baffle 218 in the vessel 202 by making contact with the inner walls of vessel opening 204. Further, after the vessel 202, vessel receptacle 206, and baffle 218 are assembled (as illustrated in FIG. 2D), baffle 218 is aligned with the vessel 202 in both horizontal and vertical directions and the baffle arms are placed in a particular position relative to the walls of the vessel. Further, as illustrated in FIG. 2D, after vessel 202, vessel receptacle 206, and baffle 218 are assembled, baffle opening 224 allows one or more pipettes to be inserted into the vessel 202 while the baffle 218 is integrated into the vessel 202 via vessel opening 204.

Figure 2E:
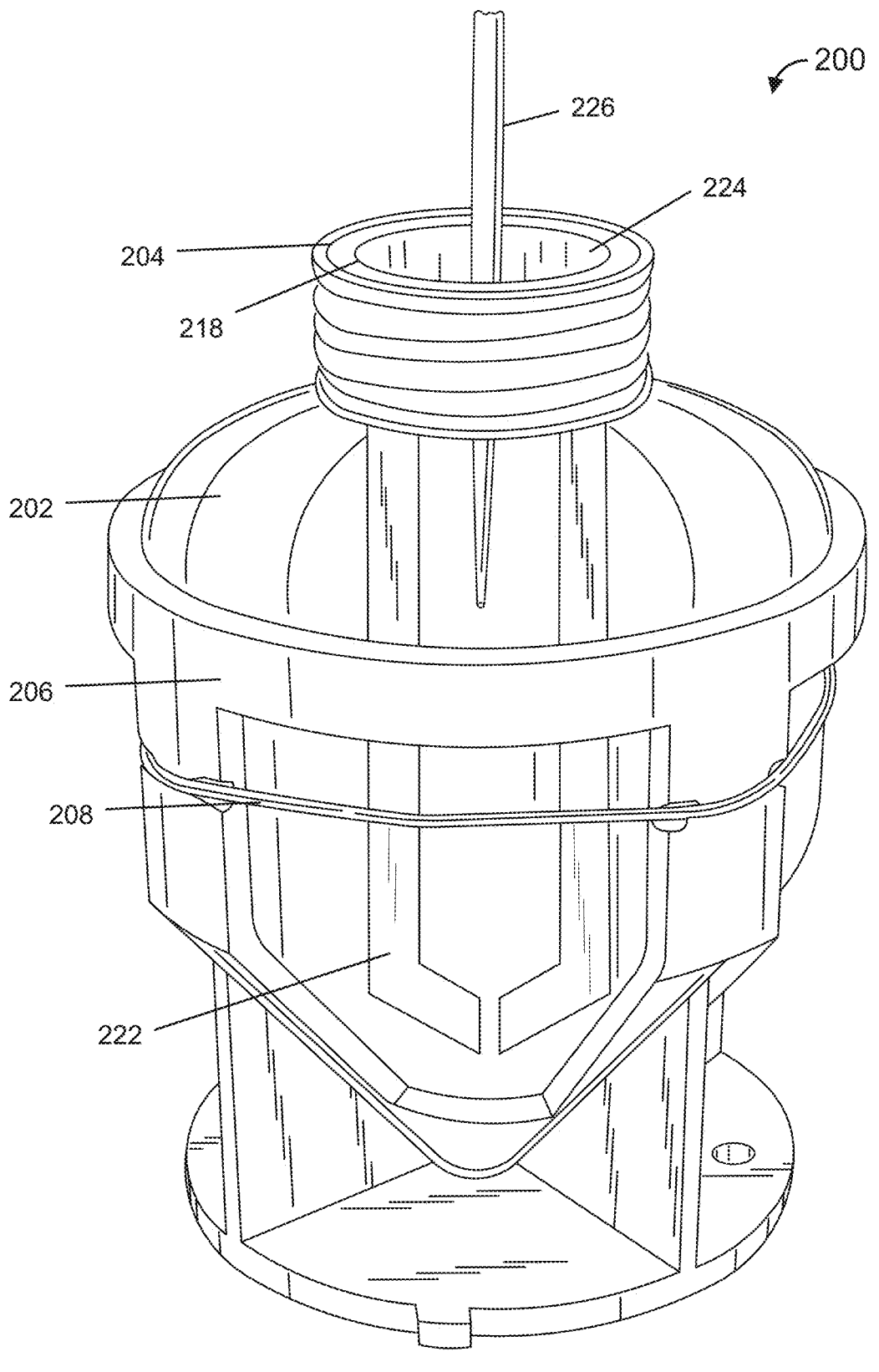
FIG. 2E illustrates the vessel and vessel receptacle of FIGS. 2A, 2B, 2C, and 2D, and a pipette according to an example embodiment.

Specifically, turning to FIG. 2E, the vessel 202, vessel receptacle 206, and baffle 218 assembly of FIG. 2D is illustrated with a pipette 226 inserted into the baffle opening 224 and extending into the body of the vessel 202 (and thereby into any solution contained in vessel 202). In FIG. 2D, in an example embodiment, pipette 226 inserted into the baffle opening 224 and extending into the body of the vessel 202 (and thereby into any solution contained in vessel 202) during a mixing event and/or solution agitation. For example, the pipette 226 may be inserted into the vessel 202 while the vessel 202 is being rotated via vessel receptacle 206, which in turn may allow pipette 226 to withdraw an aliquot of solution containing one or more particles at a particular homogenization of the particles throughout the solution (i.e., while the baffle is agitating the solution during the rotation of the vessel 202).

In examples, the mixer 214 and pipette 226 are part of a solution preparation system which includes a computing device, such as computing device 100. As described above, a computing device 100 can be implemented as a controller, and a user of the controller can use the controller to control the mixer 214 and pipette 226. The mixer 214 and pipette 226 communicably coupled with a controller, such as computing device 100, and may communicate with the controller by way of a wired connection, a wireless connection, or a combination thereof.

In examples, the controller can execute a program that causes the mixer 214 and and/or pipette 226 to perform a series of actions by way of a non-transitory computer-readable medium having stored program instructions. These program instructions include, for example, mixer 214 mixing at one or more particular speeds (e.g., rotational velocity), mixing patterns, and/or pipette 226 depth with respect to the vessel 202 and/or the solution within the vessel 202. Certain mixing speeds, mixing patterns, and pipette placement may more effectively agitate the solution to produce more consistent particle counts than other mixing speeds, patterns, and pipette tip positions.

For example, the controller program instructions can include rotating a vessel receptacle 206 connected to the mixer (and thereby the vessel 202 and/or baffle 218) at a first predetermined speed while the vessel 202 contains a solution. This first predetermined speed corresponds to a first agitating event of the solution in the vessel. Further, in practice, rotating the vessel receptacle 206 at this first predetermined speed may suspend a plurality of particles (e.g., paramagnetic beads and/or polystyrene particles) within the solution at a particular homogenization throughout the solution.

Further, in some examples, the program instructions can include rotating a vessel receptacle 206 connected to the mixer (and thereby the vessel 202 and/or baffle 218) at various mixing speeds, over a variety of mixing patterns (e.g., alternating clockwise/counterclockwise rotational patterns, etc.). Furthermore, the program instructions can include rotating a vessel receptacle 206 and agitating the vessel 202 and solution within a predetermined range of mixing speeds. For example, in one embodiment, the program instructions may include rotating a vessel receptacle 206 at a mixing speed between about 180 revolutions per minute (rpm) and about 220 rpm in an alternating clockwise clockwise/counterclockwise rotational pattern. In a further aspect, in example embodiments, the program instructions may include rotating the vessel in one direction for a predetermined time period and/or for a predetermined number of rotations (e.g., two rotations in a clockwise direction) and the rotating the vessel in another direction for a predetermined time period and/or for a predetermined number of rotations (e.g., two rotations in a counterclockwise direction). As described in more detail with respect to FIGS. 3A-3B, this mixing speed range and/or pattern may be desirable to suspend the particles without forming bubbles in the solutions, which could negatively impact the homogenization of the particles suspended throughout the solution and eventually any assays based thereon.

In some embodiments, the controller may also cause the pipette 226 to be positioned such that the corresponding pipette tip is at a first predetermined depth within vessel 202 during the agitation and withdrawing. This predetermined depth may correspond to the volume of solution within the vessel 202. For example, the predetermined depth may be at or near the vertical center of the solution which may more effectively agitate the solution to produce more consistent particle counts for the particles in the solution (e.g., paramagnetic bead counts).

As these withdrawing events are performed in a sequence, in some examples, the pipette may be configured to withdraw a predetermined volume of the solution from within the vessel 202 at the first predetermined depth. Without being bound by theory, reducing the volume of the solution reduces the height of the top of the solution within the vessel 202, and understanding the geometry of the vessel 202, withdrawing a predetermined volume of the solution will lower the top of the solution to a first predetermined height in the vessel 202. Knowing this predetermined height and/or withdrawing a predetermined volume may be beneficial for aligning the end of the pipette tip to at or near the vertical and/or horizontal center in subsequent withdrawing events.

In this way, the predetermined depths correspond to the parameters of a series of withdrawing events, such as the volume of solution within the vessel 202 during a withdrawing event. In particular, one or more predetermined depths of the end of the pipette tip in the solution correspond to the one or more volumes of solution withdrawn over a series of withdrawing events. As described above it is often desirable to position the end of the pipette tip at or near the vertical center of the solution, as well as position the end of the pipette tip at or near the horizontal center of the solution. For example, the volume of solution will decrease after each withdrawing event and one or more predetermined depths correspond to the anticipated vertical center of the solution after a predetermined volume of solution is removed from the vessel 202 after each withdrawing event.

In embodiments, the anticipated vertical center of the solution may correspond to the anticipated vertical center of the solution at the beginning of the withdrawing event. In other examples, the anticipated vertical center of the solution may correspond to the anticipated vertical center of the solution at the conclusion of the withdrawing event. In other examples, the anticipated vertical center of the solution may correspond to the anticipated vertical center of the solution at the conclusion of a particular withdrawing event in a series of withdrawing events (e.g., the vertical center of the solution after a first withdrawing event in a series of two withdrawing events). In any event, positioning the end of the withdrawing tip of the pipette at or near the center of the solution positions the pipette tip to provide consistent agitation of the solution, including any particles therein, which is desirable for consistent solution preparation and transfer of one or more aliquots of the prepared solution for further use (e.g., in assays).

In embodiments, the controller may cause the pipette 226, during the agitating to withdraw a predetermined volume of solution. This predetermined volume of solution may determine the position of pipette 226 for subsequent withdrawing events.

This sequence of agitation and withdrawing of the solution may be repeated a number of times. For instance, in some examples, during a second agitating event, the controller may cause the mixer 214 to rotate a vessel receptacle 206 connected to the mixer (and thereby the vessel 202 and/or baffle 218) at a second predetermined speed while the vessel 202 contains a solution. Additionally, during this second agitating event, the end of the pipette tip may be positioned at a second predetermined depth within the vessel 202. In some examples, the first predetermined depth is the same as the second predetermined depth. Alternately, in some examples, this second predetermined depth is different from the first predetermined depth. Namely, each predetermined depth corresponds to the volume of solution left in the vessel 202. Because there will be less solution of in vessel 202 after each corresponding agitation and withdrawing event, successive predetermined depths may be positioned lower within the vessel over successive withdrawing events.

This process may be repeated for subsequent withdrawing events. Namely, the controller may cause the mixer 214 to agitate the solution by rotating a vessel receptacle 206 connected to the mixer (and thereby the vessel 202 and/or baffle 218) and simultaneously withdraw an aliquot of solution using the pipette 226 repeatedly. Each withdrawing in a series may be performed at the same mixing speed, mixing pattern, pipette tip depth, and/or withdraw the same volume of solution. Alternatively, these various settings may change between each agitation and/or withdrawing event in a series.

Additionally, in some example embodiments, the one or more components of the controller may provide feedback to a user/operator. For example, the controller may provide an alert signal (e.g., via a user interface of the controller and/or the mixer) to provide an indication to the user that the mixing speeds are outside of a predetermined range (e.g., if the mixing speed of the mixer is below about 180 rpm or above about 220 rpm) and/or if there are other issues presented during a series of withdrawing events (e.g., if the solution left in the vessel 202 has gone below a predetermined threshold of volume). Other examples are possible.

For example, now referring to FIGS. 3A-3F, several example embodiments are shown for additional or alternative solution preparation systems 300, all of which include vessel 302 and a vessel opening 304, according to example embodiments. In the example embodiments illustrated in FIGS. 3A-3F, each vessel depicted may integrate with a vessel receptacle and/or mixer configured to hold a vessel 302 (although neither a vessel receptacle nor a mixer are specifically illustrated in any of FIGS. 3A-3F).

Figure 3A:
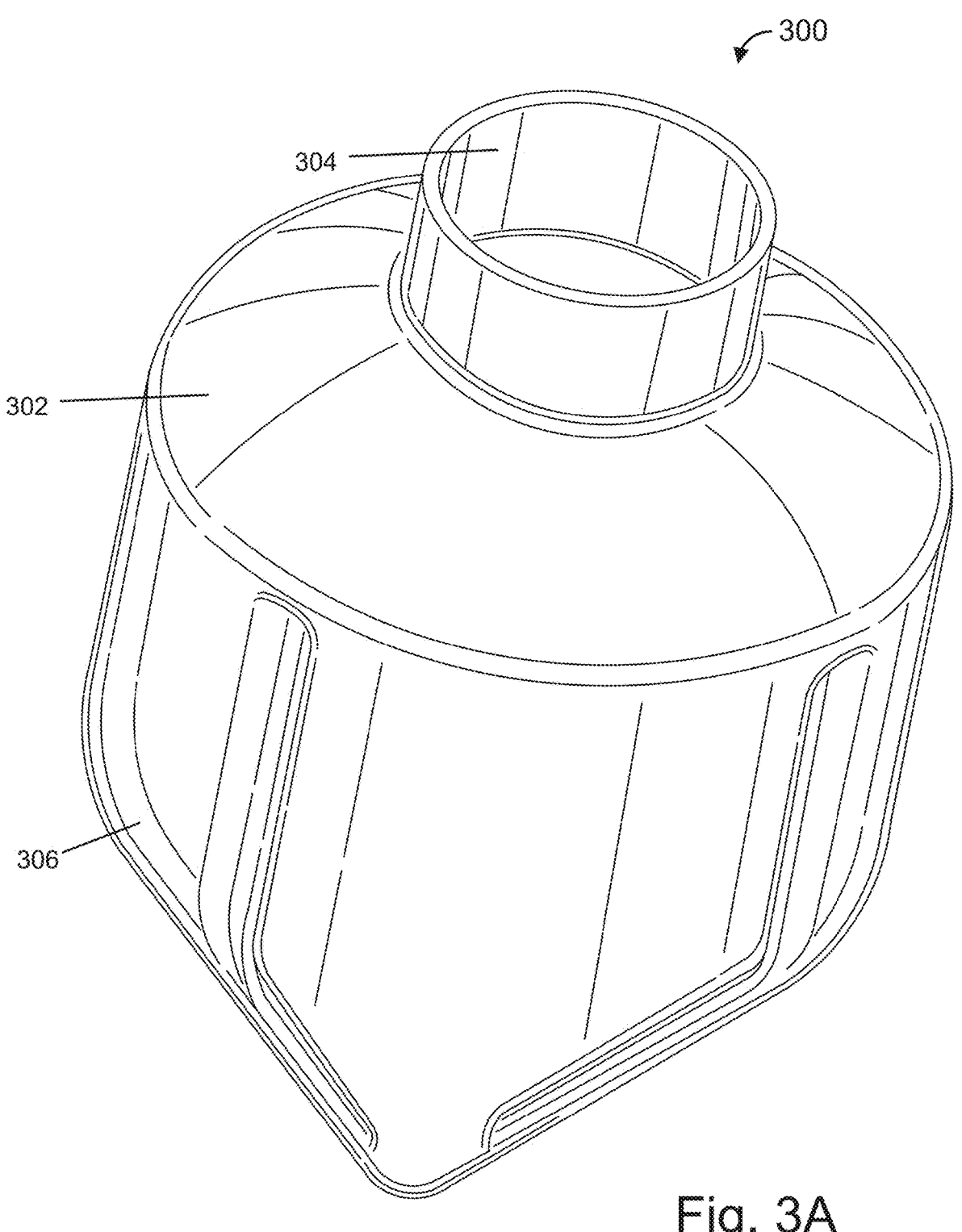
FIG. 3A illustrates a vessel and integrated baffle, according to an example embodiment.

Turning to FIG. 3A, vessel 302 contains a plurality of integrated baffles 306 that are monolithic with the interior walls of vessel 302. Although integrated baffles 306 are illustrated in FIG. 3A as integrated into the specific shape of a portion of the vessel, it should be apparent to one of skill in the art that the integrated baffles 306 could be adjusted in one or more manners depending on the vessel type, size, shape, etc. (e.g., in vessels of different circumferences and/or shapes). For example, as illustrated in FIG. 3A, the integrated baffles 306 follow the wall through the midsection of the vessel 302 and terminate in an angled portion that maps the contours of the bottom of vessel 302. In example embodiments, the integrated baffles 306 may be taller or shorter and/or cover different portions of the vessel 302 than those shown in the embodiment illustrated in FIG. 3A.

Additionally, in example embodiments, there may be more or fewer integrated baffles 306 than illustrated in FIG. 3A.

The vessel opening 304 and/or integrated baffles 306 may be configured to accommodate different types of pipettes and/or pipette tips. In some examples, the vessel opening 304 allows one or more pipettes to be inserted into the vessel 302 while the integrated baffles 306 are integrated into the vessel 302. In example embodiments, vessel opening 304 may be adjusted to accommodate different types of pipettes and/or pipette tips and/or further stabilize the one or more pipettes in relation to the vessel 302 and/or the integrated baffles 306 during withdrawing events. Other examples are possible.

Figure 3B:
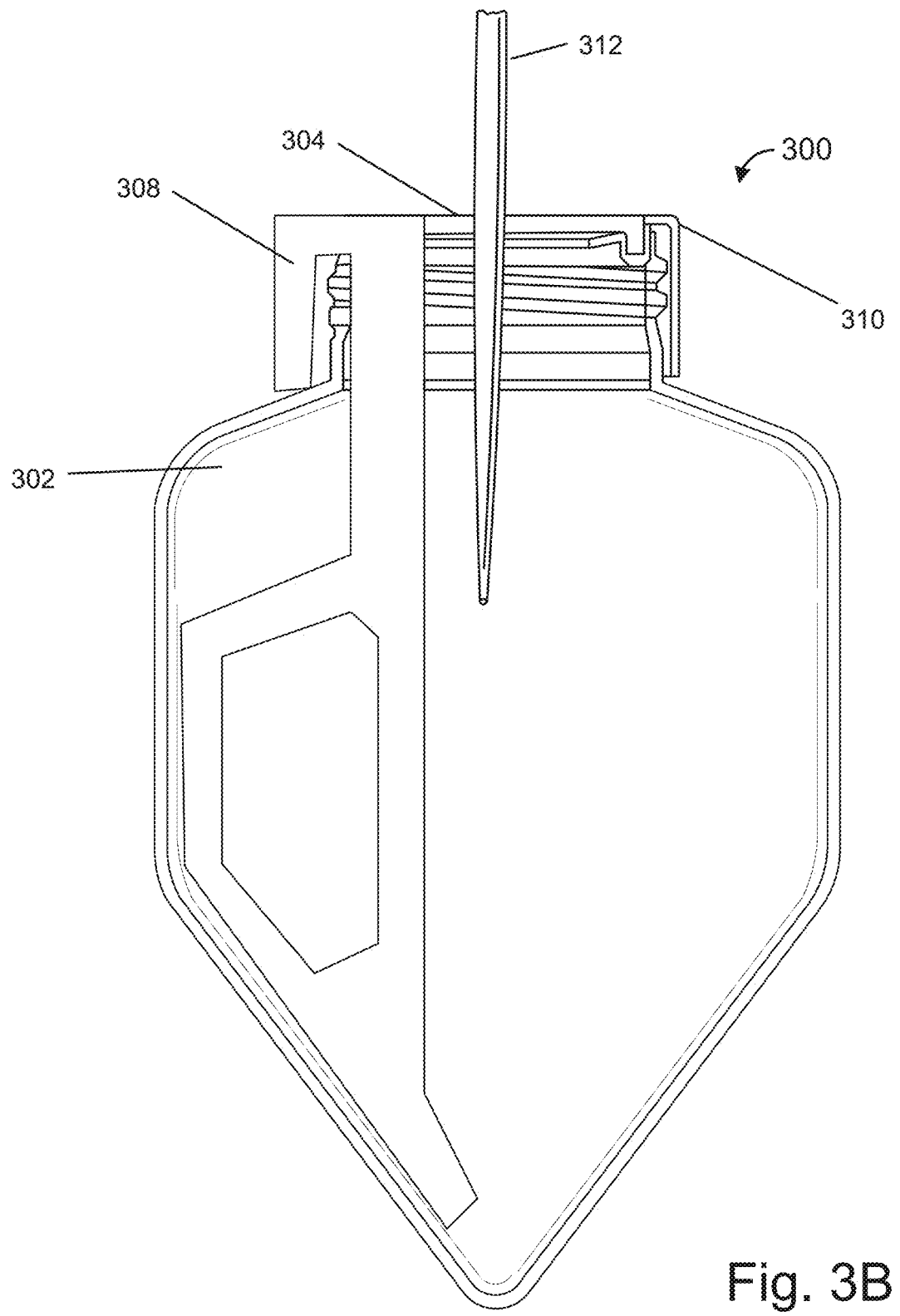
FIG. 3B illustrates a vessel, baffle, and pipette according to an example embodiment.

For example, turning to FIG. 3B, vessel 302 contains a baffle 308 monolithic with a baffle connector 310 that screws onto the vessel 302 and provides a baffle opening, through which pipette 312 may be inserted during an agitation event. Although baffle 308 is illustrated in FIG. 3B as a specific shape following the contours of a portion of the vessel, it should be apparent to one of skill in the art that the baffle 308 could be adjusted in one or more manners depending on the vessel type, size, shape, etc. (e.g., for vessels of different sizes and/or shapes).

In other example embodiments, baffle connector 310 may be configured to securely position the baffle 308 in relation to the vessel 302, so that when the vessel 302 is rotated, the baffle 308 rotates directly in proportion to the vessel 302. In other examples, however, baffle connector 310 may be configured to move the baffle 308 in relation to the vessel 302, so that when the vessel 302 is rotated, the baffle 308 rotates indirectly (or not at all) in proportion to the vessel 302. In examples, the baffle connector 310 may be taller or shorter than the embodiments illustrated in FIG. 3B (e.g., to improve the rigidity and/or grip of the baffle connector 310 on the vessel in which the baffle is inserted). Other examples are possible.

In an example, the vessel 302 may define the vessel opening 304 according to a specific circumference, which may be approximate to the circumference of the baffle connector 310. Additionally or alternatively, in an example embodiment, upon inserting the baffle 308 into the vessel 302 via vessel opening 304, the baffle connector 310 may secure the baffle 308 in the vessel 302 by making contact with outer walls of vessel opening 304, the inner walls of vessel opening 304, or both. Further, although the baffle connector 310 is illustrated in FIG. 3B as a cap integrated into the top portion of vessel 302 in FIG. 3B, the baffle connector 310 may be configured in additional or alternative manners, including by adding an additional baffle 308 and/or using different materials and/or connection mechanisms for baffle connector 310.

Additionally, in examples, baffle connector 310 may be lined with a rubber and/or foam that might allow the baffle 308 to more securely seat in the vessel 302 and/or the vessel opening 304 as compared to baffle connector 310 that do not include a liner. Additionally, these materials lining the baffle connector 310 may absorb one or more mechanical actions of the mixer, vessel, baffle, or other components, thereby reducing transfer of mechanical energy to the vessel during withdrawing events.

In a further aspect, in example embodiments, the baffle 308 may be made of one more materials, depending on the solution into which the baffle 308 is to be inserted. For example, baffle 308 may be made of one or more non-stick materials so that one or more particles in the solution do not interact with and/or stick to the baffle 308 during mixing. Additionally or alternatively baffle 308 may be made of one or more materials that interact with one or more characteristics of the one or more particles in the solution. For example, if the particles are magnetic or paramagnetic, baffle 308 may be made of a material that repels the one or more particles (or at least does not interact with the particles, magnetically) in the solution during mixing. Other examples are possible.

In an example embodiment, upon inserting the baffle 308 into the vessel 302 via vessel opening 304, the baffle 308 may be connected to the vessel 302 so that when the vessel is rotated, the baffle 308 move in the direct rotational pattern of the vessel 302. By doing so, the baffle 308 may agitate any solution and/or particles contained in the vessel 302 during agitation. In a further aspect, the baffle 308 may be connected to the baffle connector 310 using hardware that allows the baffle 308 to be adjusted in relation to baffle connector 310 and/or the vessel 302. In other examples, the baffle 308 may be non-detachably coupled to the baffle connector 310 (e.g., the baffle 308 and baffle connector 220 may a single monolithic piece).

In other examples, baffle connector 310 and baffle 308 may be configured to not move in relation to the vessel 302, so that when the vessel 302 is rotated, the baffle 308 rotate indirectly (or not at all) in proportion to the vessel 302. For example, there may be a set of ball bearings disposed between the baffle 308 and the baffle connector 310 such that when the vessel 302 is rotated, the baffle 308 remain stationary (or substantially stationary) in relation to the motion of the vessel 302.

Additionally or alternatively, the baffle 308 and/or baffle connector 310 may be configured (or adjustable) to accommodate different types of pipettes 312 and/or pipette tips. In some examples, the baffle 308 and/or baffle connector 310 may contain an opening that allows one or more pipettes 312 to be inserted into the vessel 302 while the baffle 308 and/or baffle connector 310 are integrated into the vessel 302 via vessel opening 304. In example embodiments, the baffle 308 and/or baffle connector 310 may be adjustable to accommodate different types of pipettes 312 and/or pipette tips and/or further stabilize the one or more pipettes 312 in relation to the vessel 302 and/or the baffle 308 during withdrawing events. Other examples are possible.

For example, turning to FIGS. 3C-3F, vessel 302 integrates with an expandable baffle 314 via vessel opening 304 and provides a baffle opening, through which a pipette 312 may be inserted during an agitation event. In the example embodiments illustrated in FIGS. 3C-3F, although expandable baffle 314 is illustrated as a specific shape following the contours of a portion of the vessel, it should be apparent to one of skill in the art that the expandable baffle 314 could be adjusted in one or more manners depending on the vessel type, size, shape, etc. (e.g., for vessels of different sizes and/or shapes).

Figure 3C:
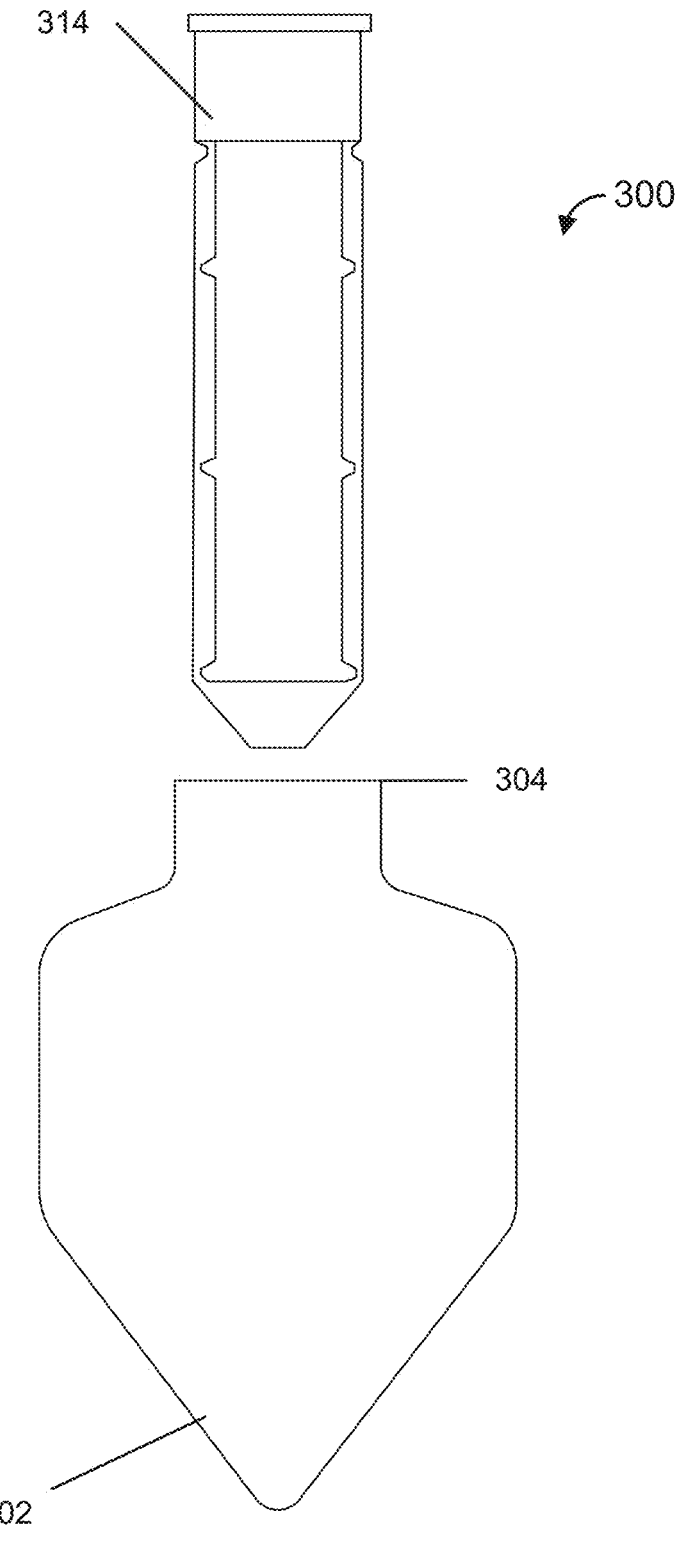
FIG. 3C illustrates a vessel and baffle according to an example embodiment.

In the example embodiments illustrated in FIGS. 3C-3F, the vessel 302 may define the vessel opening 304 according to a specific circumference, which may be approximate to the circumference of the expandable baffle 314, as illustrated in FIG. 3C.

Figure 3D:
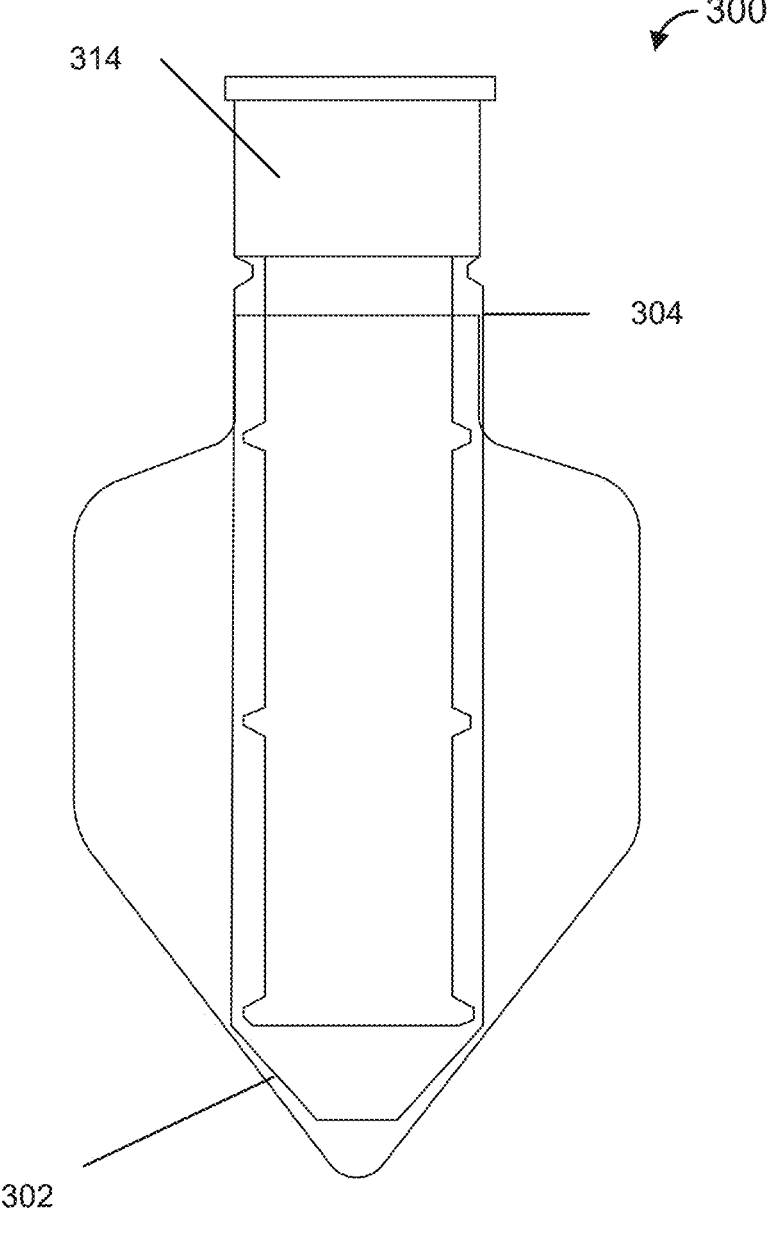
FIG. 3D illustrates the vessel and baffle of FIG. 3C, according to an example embodiment.

Turning to FIG. 3D, in an example embodiment, upon inserting the expandable baffle 314 into the vessel 302 via vessel opening 304, the expandable baffle 314 may make contact with the bottom most portion of the vessel 302.

Figure 3E:
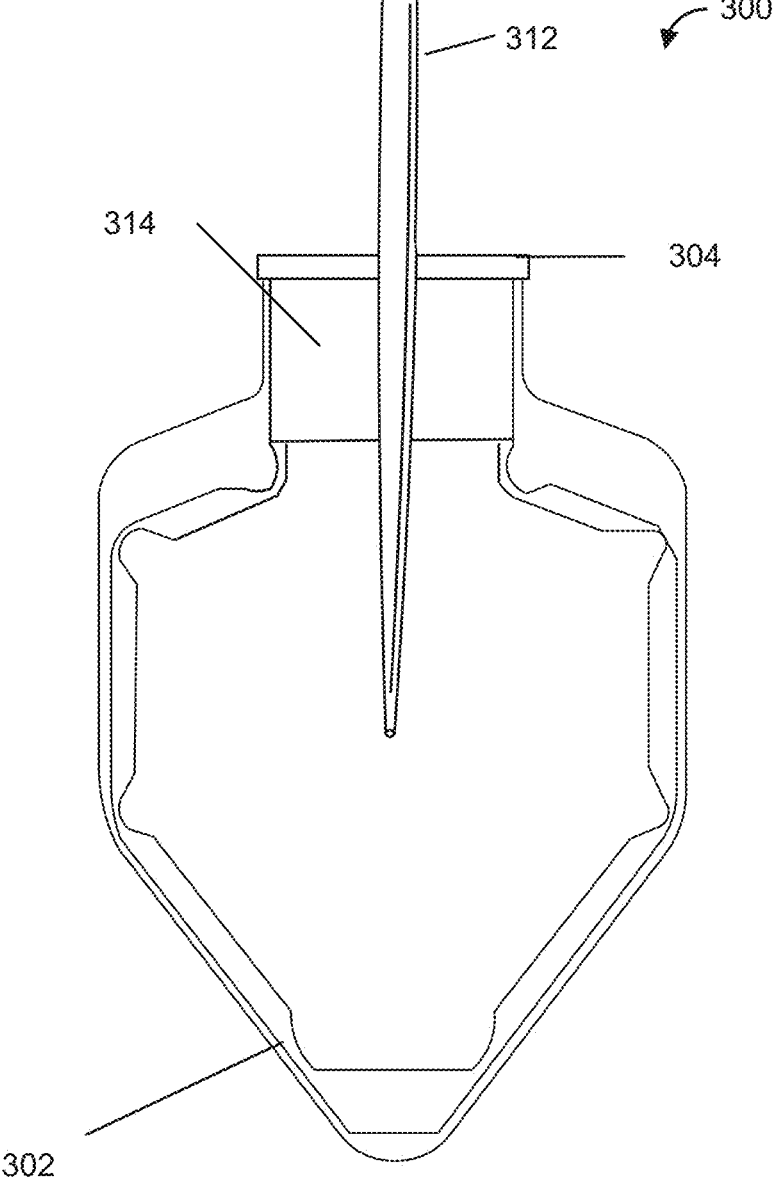
FIG. 3E illustrates the vessel and baffle of FIGS. 3C and 3D and a pipette, according to an example embodiment.
Figure 3F:
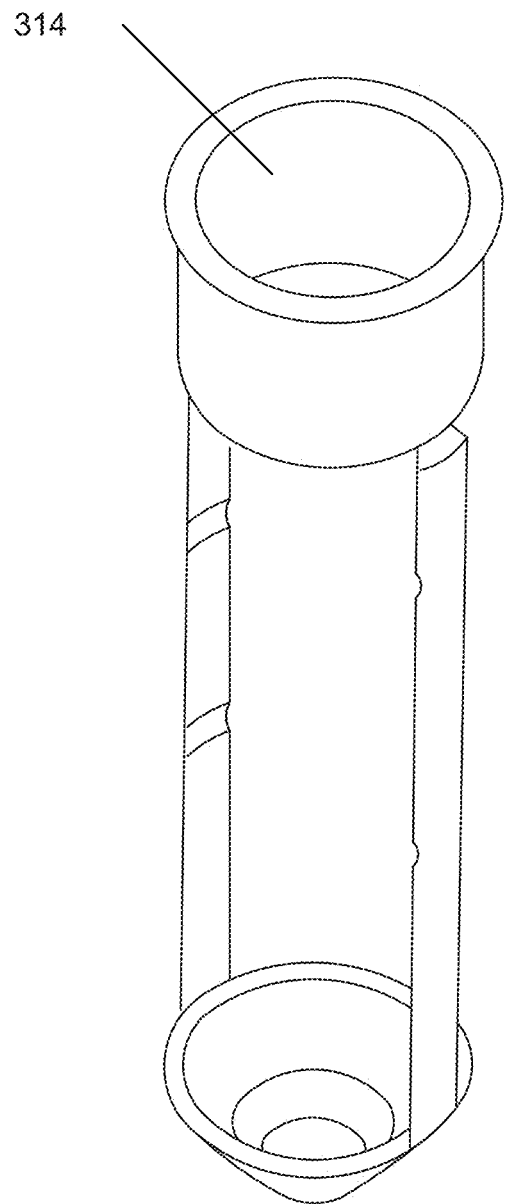
FIG. 3F illustrates the baffle of FIGS. 3C, 3D, and 3E in isolation, according to an example embodiment.

Turning to FIG. 3E, once the expandable baffle 314 makes contact with the bottom most portion of the vessel 302, the expandable baffle may be pressed further into the vessel 302, which may cause the expandable baffle 314 to expand inside of the vessel 302 and follow the contours and/or make contact with one or more of the walls of the vessel 302. In an example embodiment, as the expandable baffle 314 is pressed further into the vessel 302, the expandable baffle 314 may further seat itself around the vessel opening 304 at the top most portion of the illustrated expandable baffle 314.

In a further aspect, in example embodiments, the expandable baffle 314 may be made of one more materials, depending on the solution into which the expandable baffle 314 is to be inserted. For example, expandable baffle 314 may be made of one or more non-stick materials so that one or more particles in the solution do not interact with and/or stick to the baffle expandable baffle 314 during mixing and/or the expandable baffle 314 may be easier to insert and/or remove from the vessel between agitation events. Additionally or alternatively expandable baffle 314 may be made of one or more materials that interact with one or more characteristics of the one or more particles in the solution. For example, if the particles are magnetic or paramagnetic, expandable baffle 314 may be made of a material that repels the one or more particles (or at least does not interact with the particles, magnetically) in the solution during mixing. Other examples are possible.

Additionally or alternatively, the expandable baffle 314 may be configured (or adjustable) to accommodate different types of pipettes 312 and/or pipette tips. In some examples, the expandable baffle 314 may contain an opening that allows one or more pipettes 312 to be inserted into the vessel 302 while the baffle 308 and/or baffle connector 310 are integrated into the vessel 302 via vessel opening 304. In example embodiments, the baffle 308 and/or baffle connector 310 may be adjustable to accommodate different types of pipettes 312 and/or pipette tips and/or further stabilize the one or more pipettes 312 in relation to the vessel 302 and/or the baffle 308 during withdrawing events. Other examples are possible.

In a further aspect, to evaluate the efficacy of homogenizing a solution containing a plurality of particles one or more of the example embodiments described above, one or more devices, systems, or methods may be employed.

For example, if particles in a prepared solution are not even distributed throughout the solution prior to a withdrawing event (e.g. because of clumping, binding/settling on the bottom or sides of the vessel in which the solution containing the particles is prepared, etc.), the particles may remain in the vessel as solution is pipetted out of the vessel. To help measure the dispersion and consistency of particles in a solution, an aliquot of the prepared solution may be transferred onto a surface (e.g., a Petri dish, a well, or the like) and a composite image of the transferred aliquot of solution may be generated. In examples, this composite image may contain a plurality of images of the transferred aliquot of solution and based on one or more attributes of this generated composite image, one or more parameters may be determined for the transferred aliquot of solution.

In FIGS. 4A-4D, a sample of solution 402 containing particles is illustrated according to an example embodiment. These particles may be utilized during one or more assay procedures, including, for example, to identify a particular type and/or subset of components within a sample. In the example embodiment illustrated in FIGS. 4A-4D, the solution 402 includes paramagnetic beads 404. In some example embodiments, each of the paramagnetic beads 404 includes a unique identifier, such as a bar code. In another example, each of the paramagnetic beads 404 includes two or more unique identifiers, such as bar codes.

In yet another example, a subset of the paramagnetic beads 404 may include one unique bar code and the remaining paramagnetic beads 404 may include two or more unique bar codes. In practice, each of these bar codes may correspond to particular information about the paramagnetic bead, the solution, and/or one or more additional parameters (including those used in an assay). For example, these unique bar codes may be utilized during one or more assay procedures to identify a particular type and/or subset of paramagnetic beads within the solution that are associated with a specific assay.

It should also be noted that although the particles illustrated in FIGS. 4A-4D involve paramagnetic beads, different shapes, amounts, and/or types of particles may be used.

It should also be noted that one or more concepts illustrated in FIGS. 4A-4D may be accomplished using a computing device, such as computing device 100. As described above, a computing device 100 can be implemented as a controller, and a user of the controller can use the controller to control the capturing of one or more images of the solution, as well as process the plurality of images to generate and/or annotate a composite image of the plurality of images.

In examples, the controller can execute a program that causes the controller and/or components operating therewith (e.g., a camera) to perform a series of actions by way of a non-transitory computer-readable medium having stored program instructions.

Figure 4A:
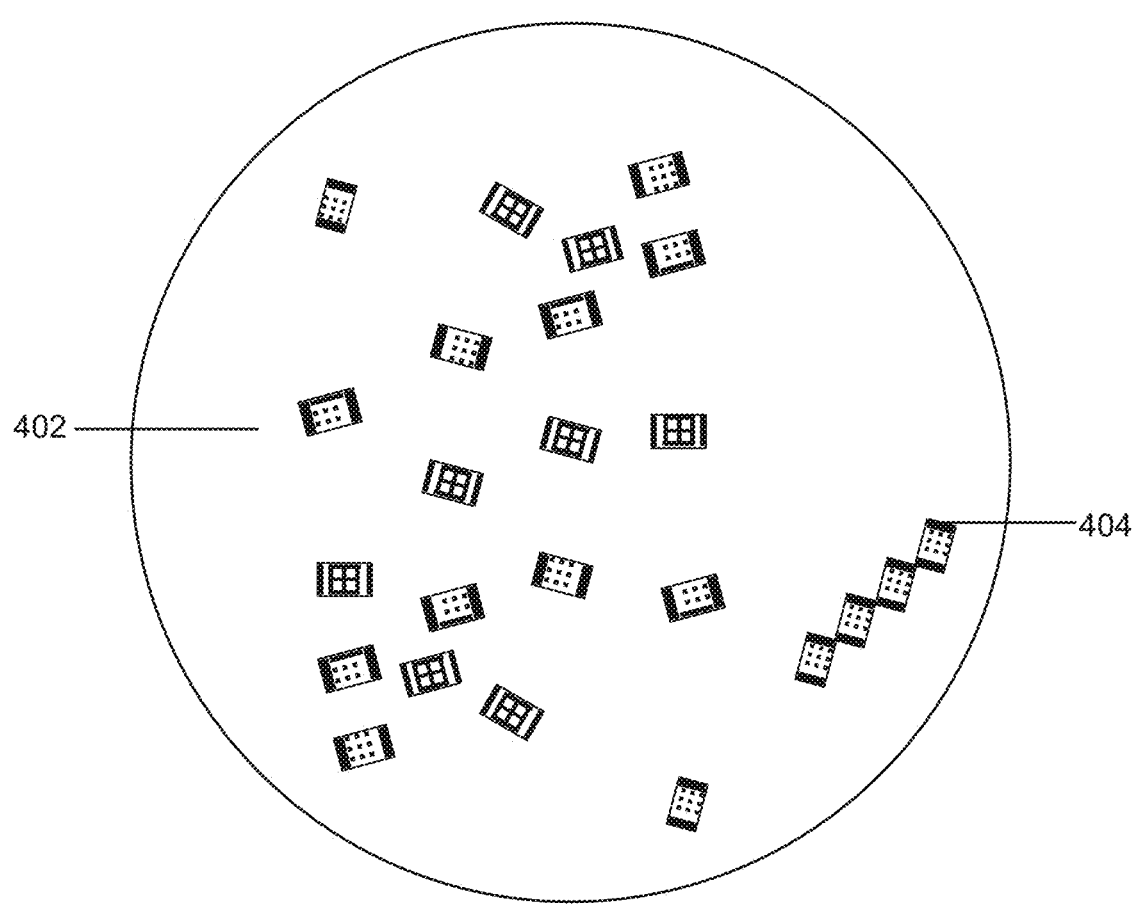
FIG. 4A illustrates a sample of solution containing particles according to an example embodiment.
Figure 4B:
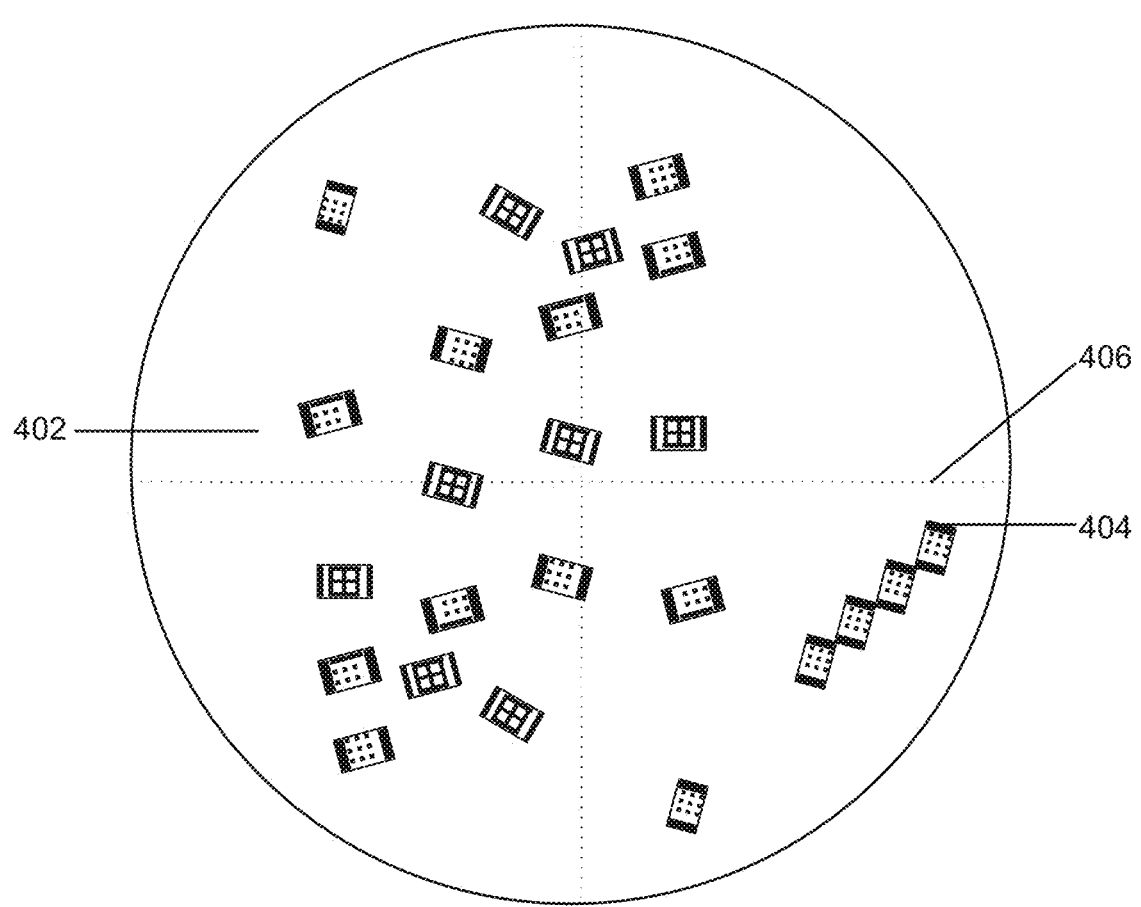
FIG. 4B illustrates an image of the sample of solution containing particles of FIG. 4A, according to an example embodiment.

In FIG. 4A, an aliquot of the prepared solution transferred onto a surface is illustrated. Turning to FIG. 4B, an example segmentation 406 of the surface is illustrated, in which the surface has been divided into four quadrants for imaging. In example embodiments, segmentation of the illustrated surface may include different sizes, shapes, numbers, and configurations of segments to be imaged for the transferred solution, depending on one or more characteristics of the sample (e.g., size, particle concentration, etc.) and/or the image analysis to be undertaken. Once the segmentation 406, one or more images may be captured for each of the one or more segments and used for further processing.

Figure 4C:
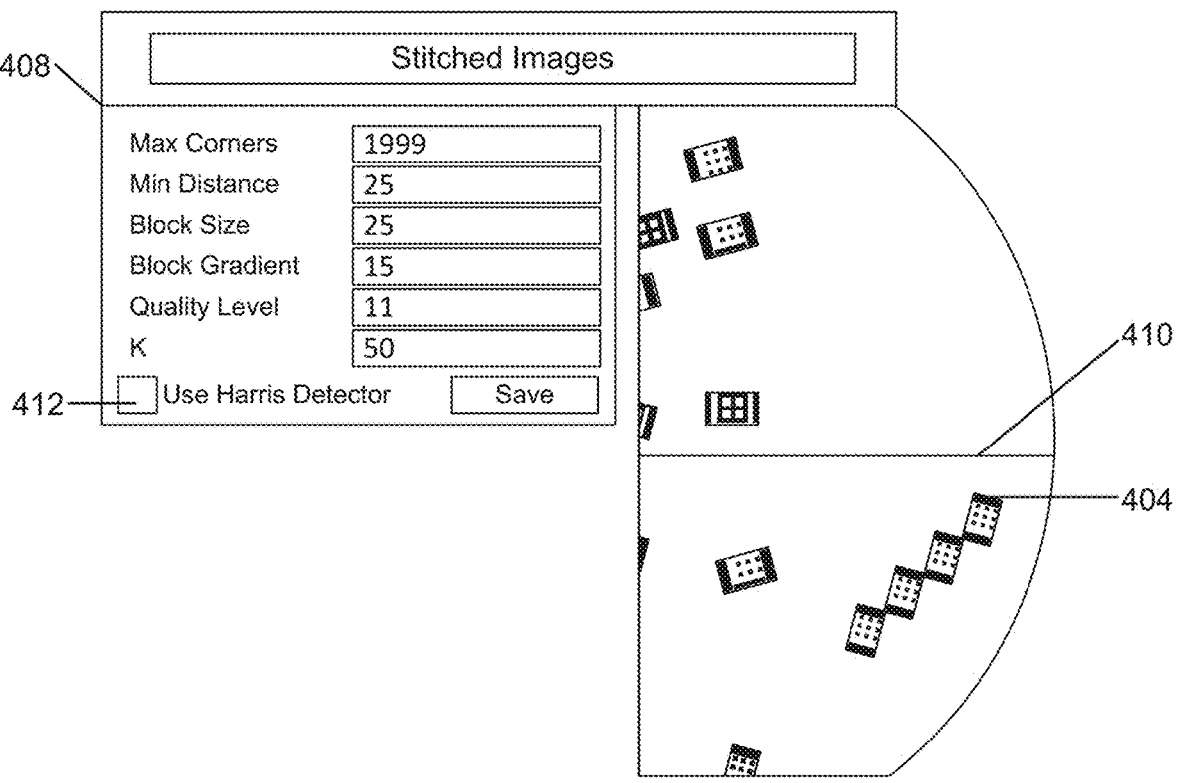
FIG. 4C illustrates a composite image of the sample of solution containing particles of FIGS. 4A and 4B and an associated graphical user interface, according to an example embodiment.

Turning to FIG. 4C, an example composite image 410 of a plurality of images captured across one or more segments of the solution is illustrated. In example embodiments, composite image 410 may be generated by stitching the plurality of images of the transferred aliquot of solution into the composite image of the transferred aliquot of solution illustrated in FIG. 4C. In example embodiments, a controller may stich together the plurality of images of the transferred aliquot of solution that contain particles and remove any images that do not contain particles. In example embodiments, the controller may determine which images in the plurality of images of the transferred aliquot of solution that contain particles by performing one or more of a pixel density and/or gradient analysis of the individual images captured by the controller. In some example embodiments, the particles in the solution (e.g., paramagnetic beads 404) may present a different contrast and/or pixel density compared the solution in which the particles are disposed (shown in FIGS. 4A-4D as the dark, black portions of paramagnetic beads 404 compared to the light, white portions of the surround solution 402). Prior to stitching, as illustrated in the example graphical user interface 408 of FIG. 4C, a user may set one or more parameters for the stitching protocol, including which images should be stitched together, as well as one or more attributes of the stitched image and/or stitching protocol (shown in FIG. 4C as "Max Corners," "Min Distance," "Block Size," "Block Gradient," "K"). Other examples are possible.

Once composite image 410 has been generated, further analysis may be undertaken on the composite image 410 to determine one or more parameters of the transferred aliquot of solution and/or the particles contained therein. In example embodiments, as shown in the example graphical user interface 408 of FIG. 4C, a user may want to determine one or more attributes of the solution, including a count of the particles in the transferred sample. To do so, the user may select to use one or more programs executing a variety of automated protocols, including one or more edge detection protocols. In an example embodiment, as illustrated in FIG. 4C, a user may select to use a Harris corner detection algorithm (shown in FIG. 4C as "Use Harris Detector" prompt 412) to perform this edge detection for the particles in the solution and thereby generate a count of the particles in the solution. In example embodiments, the controller may use one or more algorithms (including Harris corner detection) and/or protocols to detect an edge of a particle in the composite image, based at least in part on detecting an edge of the particle in the composite image, determining a presence of at least one particle in the composite image. Other examples, including the use of other image processing and/or machine learning and artificial intelligence algorithms, are possible. For example, one or more machine learning models may comprise a deep learning model and/or image pixel and/or gradient analysis models.

Figure 4D:
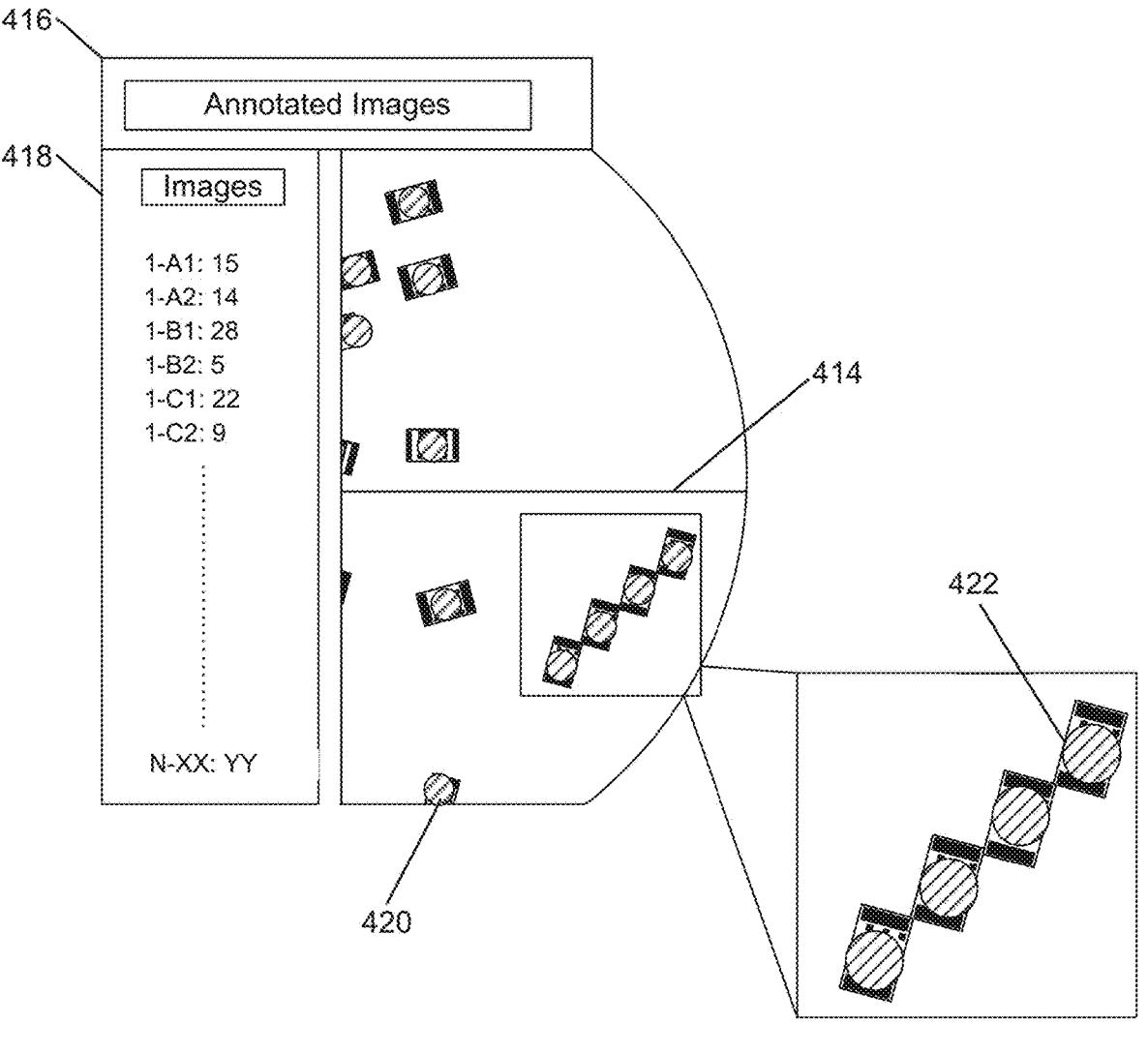
FIG. 4D illustrates an annotated version of the composite image of FIG. 4C and an associated graphical user interface, according to an example embodiment.

Turning to FIG. 4D, an example annotated image 414 of a plurality of particles detected in the composite image 410 is illustrated. In example embodiments, the controller may determine the count of the particles in solution by identifying the particles in the solution and generate annotated image 414 by utilizing one or more edge detection protocols (including the Harris corner detection algorithm). In example embodiments, the controller may perform this edge detection for the particles in the solution, generate a count of the particles in the solution, and present annotated images of the particles identified and/or counted in the annotated image 414. For example, as shown in example graphical user interface 416 of FIG. 4D, in example embodiments, the controller may present the user with an image accounting 418 of all of the images that were stitched together and/or annotated, as well as one or more attributes of the stitched image and/or stitching protocol (e.g., how many particles were identified in each image and/or segment of sample and/or corresponding images). Other examples are possible.

Once annotated image 414 has been generated, further actions may be undertaken on the annotated image 414 to further inform a user of the controller of one or more parameters of the transferred aliquot of solution and/or the particles contained therein. In example embodiments, as shown in the example graphical user interface of FIG. 4D, a user may be presented with an annotated version of a single particle 420 in the solution, as well an annotated version of a multiple particles 422 that may be overlapping and/or joined together in the solution. In example embodiments, the user may select to generate one or more additional annotated images and/or graphical user interfaces based on the annotated image 414, including total particle counts in the sample, the types of particles in the sample, and the extent of overlapping particles in the sample.

These example graphical user interfaces are merely for purposes of illustration. The features described herein may involve graphical user interfaces that are configured or formatted differently, include more or less information and/or additional or fewer instructions, include different types of information and/or instructions, and relate to one another in different ways.

EXAMPLES

To illustrate the example embodiments described above, several sample solutions were prepared and tested to measure the efficacy of the homogenization of the plurality of particles in a solution prepared in the solution preparation system described above. In example embodiments, these solutions may utilize a variety of solutions. Additionally or alternatively, these solutions may also include a mixture of particles (e.g., bar coded paramagnetic beads) with a variety of different attributes (e.g., all bar coded paramagnetic beads may comprise a single bar code or a mix bar codes). Additionally, several solutions were prepared and tested to measure the efficacy of performing a read buffer phase. Further details are provided below.

Example 1: Homogenization

In an example experiment, using the example solution preparation system 200 of FIGS. 2A-2E, a mixer was used to rotate a vessel containing 400 ml of solution (via a vessel receptacle) between 180 rpm and 220 rpm for a period of 10 seconds in an alternating clockwise/counterclockwise rotational pattern. In a first portion of the example experiment, the solution in the vessel was agitated without a baffle inserted into the vessel during agitation. In a second portion of the example experiment, the solution in the vessel was agitated with a baffle inserted into the vessel during agitation. After each agitation event, imaging was conducted to determine the homogenization of the beads in the solution.

Figure 5A:
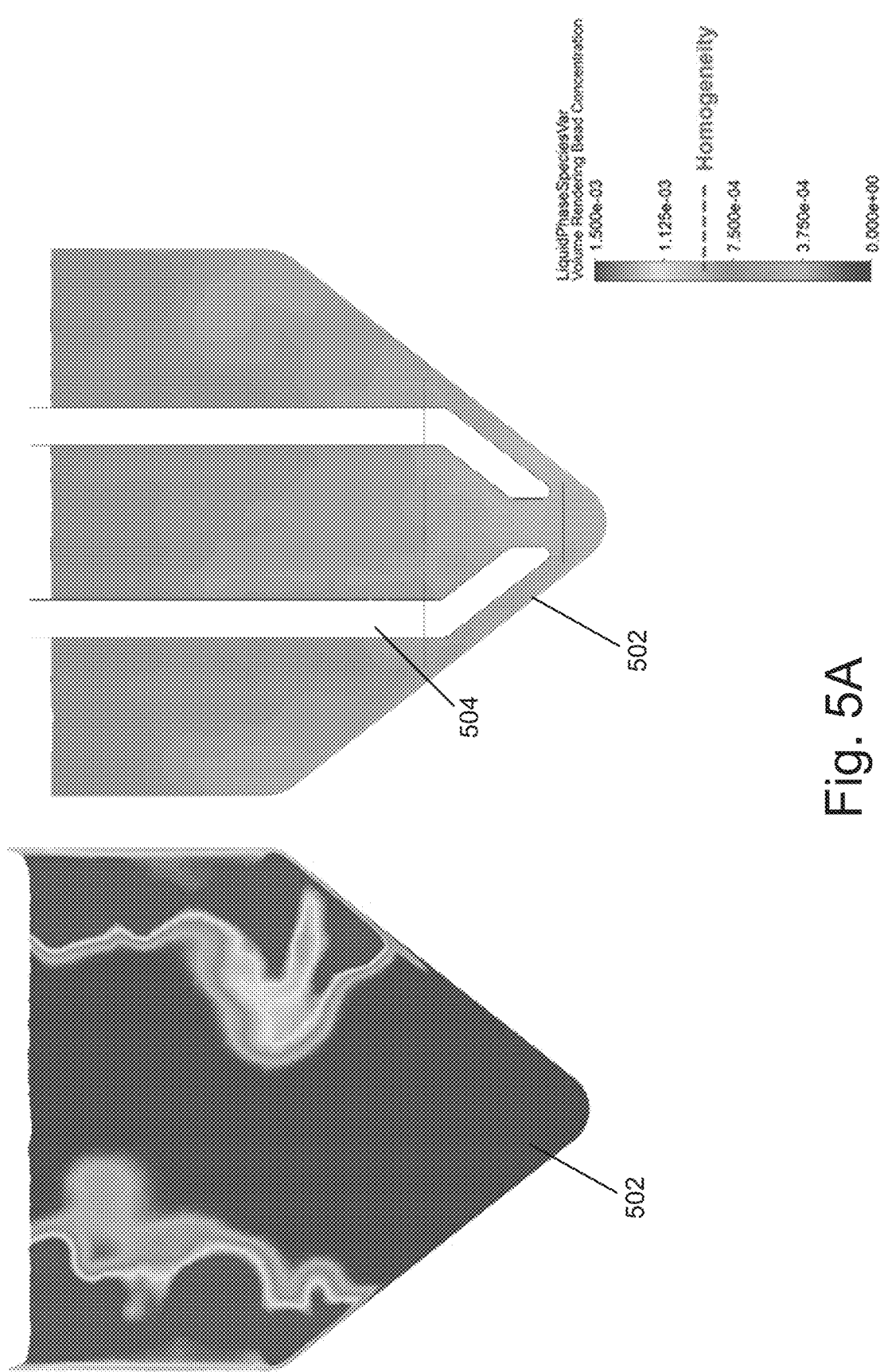
FIG. 5A illustrates particle concentration results in a solution before and after using a baffle.
Figure 5B:
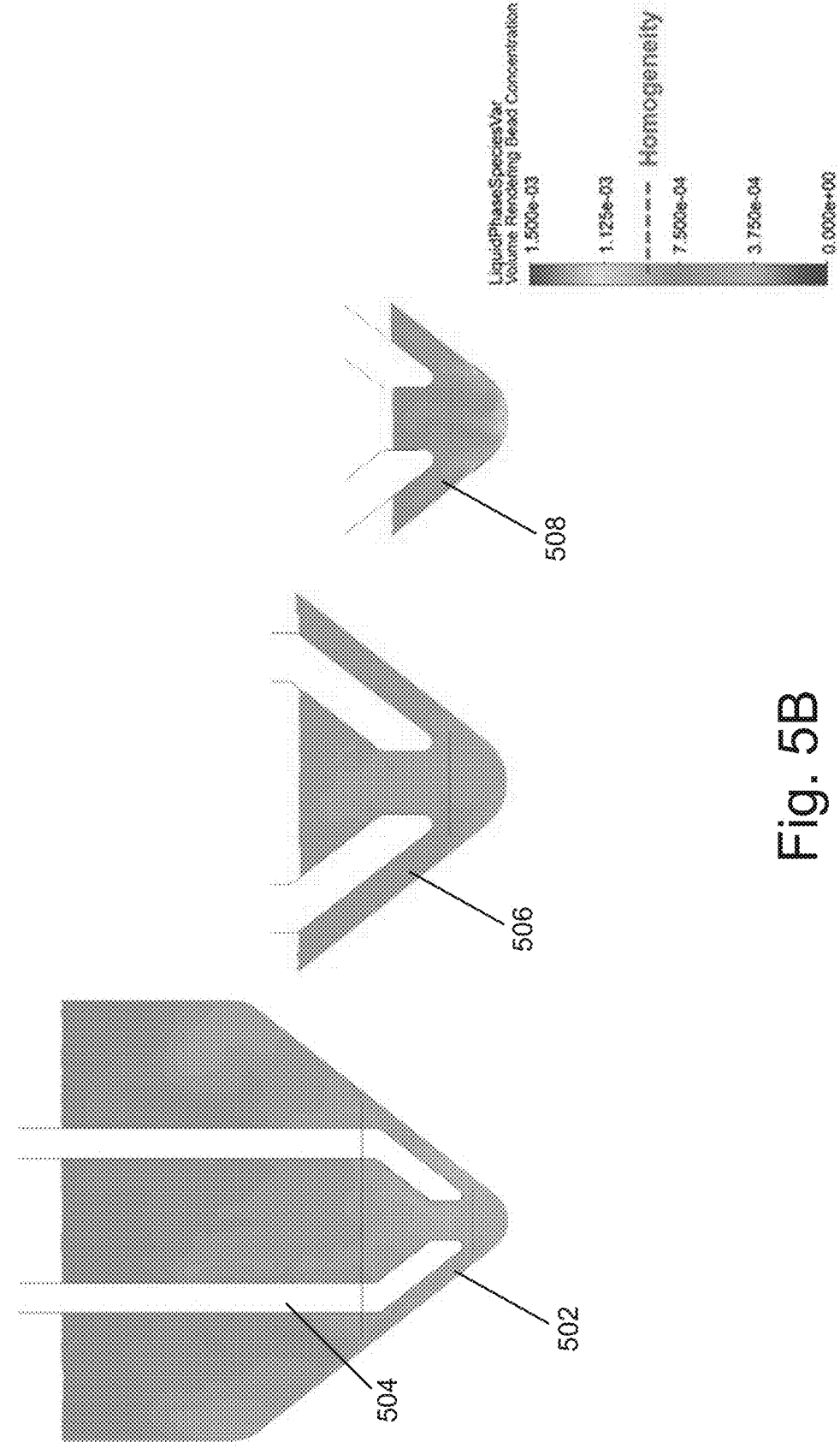
FIG. 5B illustrates particle concentration results in a solution using a baffle for varying volumes of solution.

FIGS. 5A and 5B show the results of this experiment. Namely, FIG. 5A shows the homogenization of the beads in the solution without a baffle in the vessel 502 and with a baffle 504 inserted the vessel 502.

As shown in FIG. 5A, mixing without a baffle produced a low and/or inconsistent paramagnetic bead homogenization throughout the vessel. As shown in FIG. 5A, mixing with a baffle 504 produced the most homogenous dispersion of beads throughout the solution and the vessel, and thereby the most consistent bead counts to be used in assays and/or other tests that might involve the prepared solution.

Additionally, utilizing the mixer and baffle to mix the bead solution not only improved bead count and solution homogeneity and consistency across the vessel and withdrawing events, it also saves time in the overall solution preparation procedure, which allows the user to increase throughput (whether in an automated or manual procedure) resulting in time and cost savings for the solution preparation (and assay) procedure.

Turning to FIG. 5B, FIG. 5B shows the homogenization of the beads in the solution with a baffle in the vessel 502 over a series of withdrawing events and volumes of solution remaining in the vessel to be withdrawn.

As shown in FIG. 5B, mixing with a baffle 504 produced a homogenous dispersion of beads throughout the solution, even at varying volumes of solution in the vessel. As shown in FIG. 5B, mixing with a baffle 504 in a first reduced volume of solution 506 (20 ml) in the vessel still produced a homogenous dispersion of beads throughout the solution and the vessel. As shown in FIG. 5B, mixing with a baffle 504 in a second reduced volume of solution 508 (5 ml) in the vessel produced a slightly homogenous dispersion of beads throughout the solution and the vessel. However, over all volumes of solution in the vessel, mixing with a baffle 504 produced a homogenous dispersion of beads throughout the solution and resulted in more consistent bead counts to be used in assays and/or other tests that might involve the prepared solution.

Furthermore, although the experiment in Example 1 describes particular components and tests utilized according to specific parameters, it should be understood that the claimed devices and/or methods may be implemented in a variety of scenarios, including scenarios other than the solution preparation and/or assays described herein. For example, claimed devices and/or methods may be implemented in any situation where there is a need to prepare and/or pipette a consistently homogenous solution.

Example 2: Automated Bead Count

In an example experiment, using the devices, systems, or methods of FIGS. 4A-4D, a controller and associated program instructions to determine the accuracy of an automated bead counting protocol and compare it to a manual bead counting protocol. In the first portion of the experiment, an automated bead counting protocol was used to capture, stich, and analyze images of the sample solution to determine the total number (counts) of particles in the solution sample contained in a well (e.g., a Petri dish, a well, or the like). In a second portion of the example experiment, the sample solution was analyzed manually by an operator to determine the total number (counts) of particles in the solution sample contained in a well (e.g., a Petri dish, a well, or the like), by manually counting the particles in the captured images. After the first and second portions of the experiment, the counts were compared to determine an agreement between the automated and manual bead counting protocols.

Figure 6:
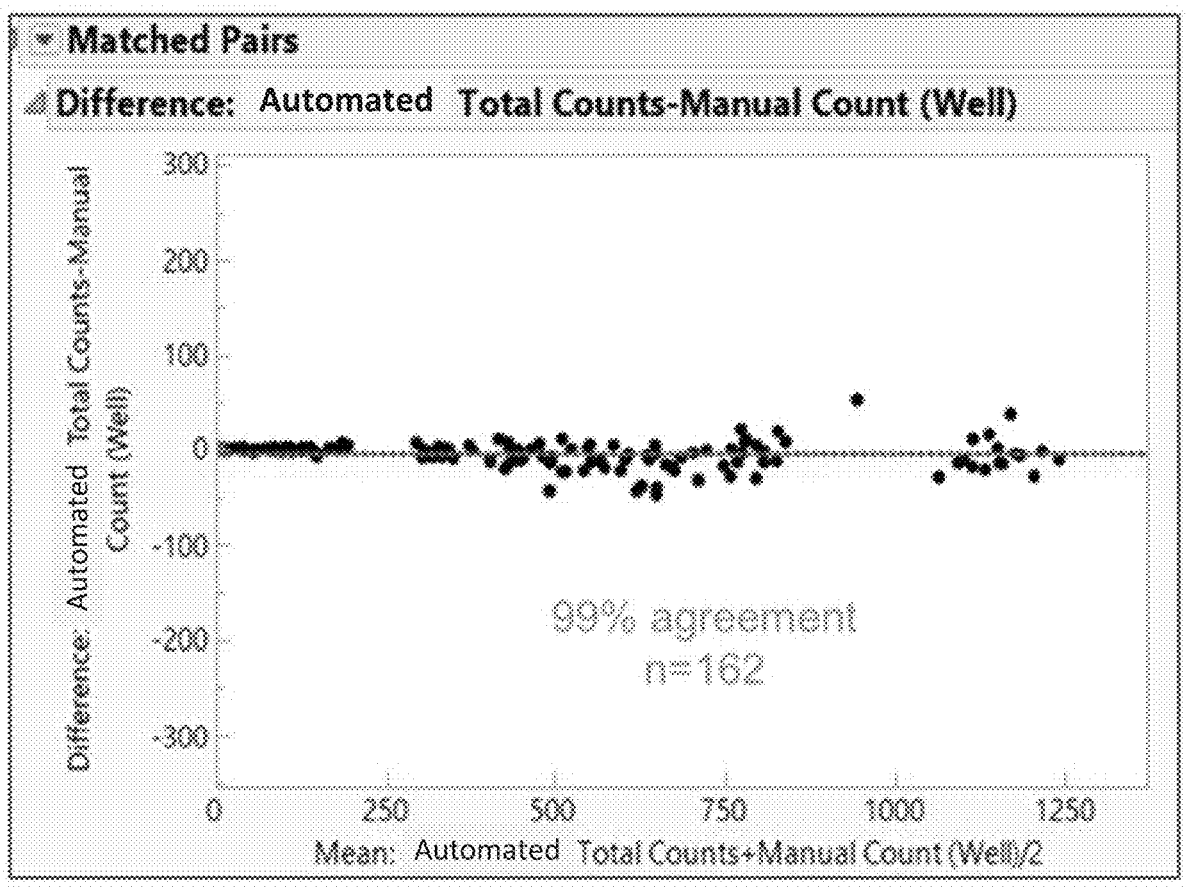
FIG. 6 illustrates particle count readings using an automated counting program compared to a manual counting protocol after a solution is prepared and an associated graphical user interface according to an example embodiment.

FIG. 6 shows the results of this experiment. Namely, FIG. 6 shows 99% agreement between the automated and manual bead counting protocols.

Additionally, utilizing automated bead counting protocols improved bead count consistency across image analysis, it also saves time in the overall bead counting protocol and solution preparation procedure, as well as ensures more consistent results in the solution preparation procedure. For example, because a user may efficiently and consistently test one or more parameters of the prepared solution (e.g., bead counts in representative samples of the prepared solution), the may user to increase the throughput (whether in an automated or manual procedure) and consistency of prepared solution, resulting in time and cost savings, as well as improved results, for the solution preparation (and assay) procedure.

Furthermore, although the experiment in Example 2 describes particular components and tests utilized according to specific parameters, it should be understood that the claimed devices and/or methods may be implemented in a variety of scenarios, including scenarios other than the solution preparation and/or assays described herein. For example, claimed devices and/or methods may be implemented in any situation where there is a need to prepare and/or pipette a consistently homogenous solution.

Example Methods and Aspects

Now referring to FIG. 7, an example method of preparing an aliquot of solution comprising a plurality of particles is illustrated. Method 700 shown in FIG. 7 presents an example of a method that could be used with the computing device 100 and/or solution preparation system 200 (or one or more components thereof) shown in FIGS. 1-4D, for example. Further, devices or systems may be used or configured to perform logical functions presented in FIG. 7. In other examples, components of the devices and/or systems may be arranged to be adapted to, capable of, or suited for performing the functions, such as when operated in a specific manner. Method 700 may include one or more operations, functions, or actions as illustrated by one or more of blocks 700-702. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

At block 702, method 700 for preparing an aliquot of solution comprising a plurality of particles involves agitating the solution with a baffle at a predetermined mixing speed to suspend the plurality of particles in the solution, wherein the baffle positioned at least partially within a vessel containing the solution, and wherein the vessel is engaged with a vessel receptacle configured to hold the vessel.

In some example embodiments, the vessel defines an opening, and the baffle extends at least partially through the opening. Additionally, in some examples, the baffle defines an opening that is aligned with an opening of a vessel. Further, in some examples, the baffle is non-detachably coupled to an interior portion of a vessel.

At block 704, method 700 involves withdrawing, during the agitating, the aliquot of solution from the vessel with a pipette, such that an end of a pipette tip is positioned within the vessel. In some examples, withdrawing, during the agitating, the aliquot of solution comprises positioning the end of the pipette tip through the opening of the baffle In examples, the plurality of particles comprise a plurality of paramagnetic beads. Additionally, in some examples, the plurality of paramagnetic beads comprise two or more unique bar codes.

Additionally, in some examples, the method 700 further includes transferring the aliquot of solution onto a surface, generating a composite image of the transferred aliquot of solution, wherein the composite image comprises a plurality of images of the transferred aliquot of solution, and, based on the generated composite image, determining a parameter of the transferred aliquot of solution. In these examples, generating the composite image of the transferred aliquot of solution further comprises stitching the plurality of images of the transferred aliquot of solution into the composite image of the transferred aliquot of solution.

Further, in some examples, determining a parameter of the transferred aliquot of solution comprises counting the plurality of particles in the transferred aliquot of solution. In these examples, counting a plurality of particles in the transferred aliquot of solution comprises: detecting an edge of a particle in the composite image and, based at least in part on detecting an edge of the particle in the composite image, determining a presence of at least one particle in the composite image.

Further, in some examples, the method 700 further includes transmitting instructions that cause a graphical user interface to display a graphical representation of the determined parameter of the transferred aliquot of solution.

In one aspect, a non-transitory computer-readable medium, having stored thereon program instructions that, upon execution by a controller, cause a controller to perform a set of operations comprising agitating a solution with a baffle at a predetermined mixing speed to suspend a plurality of particles in the solution, wherein the baffle positioned at least partially within a vessel containing the solution, and wherein the vessel is engaged with a vessel receptacle configured to hold the vessel and withdrawing, during the agitating, the aliquot of solution from the vessel with a pipette, such that an end of a pipette tip is positioned within the vessel, is disclosed.

In some example embodiments, the vessel defines an opening, and the baffle extends at least partially through the opening. Additionally, in some examples, the baffle defines an opening that is aligned with an opening of a vessel. Further, in some examples, the baffle is non-detachably coupled to an interior portion of a vessel.

In some examples, withdrawing, during the agitating, the aliquot of solution comprises positioning the end of the pipette tip through the opening of the baffle In example embodiments, the set of operations further comprises includes transferring the aliquot of solution onto a surface, generating a composite image of the transferred aliquot of solution, wherein the composite image comprises a plurality of images of the transferred aliquot of solution, and, based on the generated composite image, determining a parameter of the transferred aliquot of solution. In these examples, generating the composite image of the transferred aliquot of solution further comprises stitching the plurality of images of the transferred aliquot of solution into the composite image of the transferred aliquot of solution.

Further, in some examples, determining a parameter of the transferred aliquot of solution comprises counting the plurality of particles in the transferred aliquot of solution. In these examples, counting a plurality of particles in the transferred aliquot of solution comprises: detecting an edge of a particle in the composite image and, based at least in part on detecting an edge of the particle in the composite image, determining a presence of at least one particle in the composite image.

In example embodiments, the set of operations further comprises transmitting instructions that cause a graphical user interface to display a graphical representation of the determined parameter of the transferred aliquot of solution.

The singular forms of the articles "a," "an," and "the" include plural references unless the context clearly indicates otherwise. For example, the term "a compound" or "at least one compound" can include a plurality of compounds, including mixtures thereof.

Various aspects and embodiments have been disclosed herein, but other aspects and embodiments will certainly be apparent to those skilled in the art. Additionally, the various aspects and embodiments disclosed herein are provided for explanatory purposes and are not intended to be limiting, with the true scope being indicated by the following claims.

What is claimed is:

1. A method for preparing an aliquot of solution comprising a plurality of particles, the method comprising:
agitating the solution with a baffle at a predetermined mixing speed sufficient to suspend the plurality of particles in the solution, wherein the baffle is positioned at least partially within a vessel containing the solution, and wherein the vessel is engaged with a vessel receptacle configured to hold the vessel;

withdrawing, during the agitating, the aliquot of solution from the vessel with a pipette, such that an end of a pipette tip is positioned within the vessel;

transferring the aliquot of solution from the pipette onto a surface;

generating a composite image of the transferred aliquot of solution, wherein the composite image comprises a plurality of images of the transferred aliquot of solution; and based on the generated composite image, determining a parameter of the transferred aliquot of solution.

2. The method of claim 1, wherein the vessel defines an opening, and wherein the baffle extends at least partially through the opening.

3. The method of claim 2, wherein the baffle defines a baffle opening that is aligned with the opening of the vessel.

4. The method of claim 3, wherein withdrawing, during the agitating, the aliquot of solution comprises positioning the end of the pipette tip through the baffle opening.

5. The method of claim 1, wherein the baffle is non-detachably coupled to an interior portion of the vessel.

6. The method of claim 1, wherein the plurality of particles comprises a plurality of paramagnetic beads, and wherein the plurality of paramagnetic beads comprises one or more bar codes used to identify one or more of the plurality of paramagnetic beads in the aliquot of solution.

7. The method of claim 1, wherein generating the composite image of the transferred aliquot of solution further comprises stitching the plurality of images of the transferred aliquot of solution into the composite image of the transferred aliquot of solution.

8. The method of claim 1, wherein determining a parameter of the transferred aliquot of solution comprises counting the plurality of particles in the transferred aliquot of solution.

9. The method of claim 8, wherein counting the plurality of particles in the transferred aliquot of solution comprises:
detecting an edge of a particle in the composite image; and based at least in part on detecting an edge of the particle in the composite image, determining a presence of at least one particle in the composite image.

10. The method of claim 1, wherein the method further comprises:
transmitting instructions that cause a graphical user interface to display a graphical representation of the determined parameter of the transferred aliquot of solution.

* * * * *